(12) United States Patent
Choi et al.

(10) Patent No.: US 9,931,331 B2
(45) Date of Patent: Apr. 3, 2018

(54) PHARMACEUTICAL COMPOSITION FOR PREVENTING OR TREATING CANCER, CONTAINING PROTEASOME INHIBITOR AND LOPERAMIDE AS ACTIVE INGREDIENTS

(71) Applicant: AJOU UNIVERSITY INDUSTRY-ACADEMIC COOPERATION FOUNDATION, Suwon-si, Gyeonggi-do (KR)

(72) Inventors: Kyeong Sook Choi, Suwon-si (KR); In Young Kim, Suwon-si (KR); Mi Jin Yoon, Suwon-si (KR); A Reum Lee, Suwon-si (KR)

(73) Assignee: AJOU UNIVERSITY INDUSTRY-ACADEMIC COOPERATION FOUN DATION, Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/108,785

(22) PCT Filed: Sep. 17, 2014

(86) PCT No.: PCT/KR2014/008633
§ 371 (c)(1),
(2) Date: Jun. 29, 2016

(87) PCT Pub. No.: WO2015/102205
PCT Pub. Date: Jul. 9, 2015

(65) Prior Publication Data
US 2016/0324843 A1 Nov. 10, 2016

(30) Foreign Application Priority Data
Dec. 31, 2013 (KR) .................. 10-2013-0168439

(51) Int. Cl.
| | |
|---|---|
| *A61K 31/451* | (2006.01) |
| *A61K 31/12* | (2006.01) |
| *A61K 31/121* | (2006.01) |
| *A61K 31/19* | (2006.01) |
| *A61K 31/56* | (2006.01) |
| *A61K 31/69* | (2006.01) |
| *A61K 38/05* | (2006.01) |
| *A61K 38/07* | (2006.01) |
| *A61K 38/08* | (2006.01) |
| *A61K 38/00* | (2006.01) |

(52) U.S. Cl.
CPC .......... *A61K 31/451* (2013.01); *A61K 31/12* (2013.01); *A61K 31/121* (2013.01); *A61K 31/19* (2013.01); *A61K 31/56* (2013.01); *A61K 31/69* (2013.01); *A61K 38/005* (2013.01); *A61K 38/05* (2013.01); *A61K 38/07* (2013.01); *A61K 38/08* (2013.01)

(58) Field of Classification Search
CPC ...... A61K 31/451; A61K 31/69; A61K 31/12; A61K 31/56; A61K 31/121; A61K 31/19; A61K 38/05; A61K 38/08; A61K 38/07; A61K 38/005; A61K 2300/00
See application file for complete search history.

(56) References Cited

U.S. PATENT DOCUMENTS

2007/0161543 A1* 7/2007 Yu .......................... A61K 38/05
514/114

FOREIGN PATENT DOCUMENTS

| JP | 2008-530239 A | 8/2008 |
|---|---|---|
| KR | 10-2007-7027765 A | 1/2008 |

OTHER PUBLICATIONS

International Search Report for PCT/KR2014/008633 dated Jan. 14, 2015 from Korean Intellectual Property Office.
Helen Mackay et al., "APhase II Trialwith Pharmacodynamic Endpoints of the Proteasome Inhibitor Bortezomib in Patients with Metastatic Colorectal Cancer", Clinical Cancer Research, vol. 11, No. 15, pp. 5526-5533, 2005.
Xing Wen Gong et al., "Loperamide, an antidiarrhea drug, has antitumor activity by inducing cell apoptosis", Pharmacological Research, vol. 65, pp. 372-378, 2012.
Bret Bannerman et al., "Preclinical evaluation of the antitumor activity of bortezomib in combination with vitamin C or with epigallocatechin gallate, a component of green tea", Cancer Chemotheraphy and Pharmacology, vol. 68, pp. 1145-1154, 2011.
Kunie Hagiwara et al., "Analgesic action of loperamide, an opioid agonist, and its blocking action on voltage-dependent Ca2+ channels", Neuroscience Research, vol. 46, pp. 493-497, 2003.

* cited by examiner

*Primary Examiner* — Timothy R Rozof
(74) *Attorney, Agent, or Firm* — Revolution IP, PLLC

(57) ABSTRACT

The present invention relates to an anticancer supplement containing loperamide as an active ingredient. More specifically, a proteasome inhibitor alone cannot exhibit an anticancer effect on solid cancers and some blood cancers, but when the proteasome inhibitor and loperamide are co-administered or a composition containing the proteasome inhibitor and loperamide is provided, cancer cell death by the proteasome inhibitor can be effectively induced, thereby exhibiting an improved anticancer effect, and enhancing anticancer effects on solid cancers and blood cancers while reducing side effects caused by a high-concentration of the proteasome inhibitor. Therefore, the composition containing the proteasome inhibitor and loperamide as active ingredients, according to the present invention, can be useful for preventing or treating cancer, and loperamide can be provided as an anticancer supplement when the proteasome inhibitor is used to treat cancer.

7 Claims, 18 Drawing Sheets

*P<0.05 VS CONTROP GROUP; #P<0.05 VS BORTEZOMIB

*P<0.05 VS CONTROP GROUP; #P<0.05 VS CARFILZOMIB

*P<0.05 VS CONTROP GROUP; #P<0.05 VS MLN9708

*P<0.05 VS CONTROP GROUP; #P<0.05 VS EPOXOMICIN

*P<0.05 VS CONTROP GROUP; #P<0.05 VS CURCUMIN

*P<0.05 VS CONTROP GROUP; #P<0.05 VS CELASTROL

*P<0.05 VS CONTROP GROUP; #P<0.05 VS PROTEASOME INHIBITOR

PHARMACEUTICAL COMPOSITION FOR PREVENTING OR TREATING CANCER, CONTAINING PROTEASOME INHIBITOR AND LOPERAMIDE AS ACTIVE INGREDIENTS

CROSS REFERENCE TO PRIOR APPLICATIONS

This application is a National Stage Application of PCT International Patent Application No. PCT/KR2014/008633 filed on Sep. 17, 2014, under 35 U.S.C. § 371, which claims priority to Korean Patent Application No. 10-2013-0168439 filed on Dec. 31, 2013, which are all hereby incorporated by reference in their entirety.

TECHNICAL FIELD

The inventive concept relates to a pharmaceutical composition for preventing or treating cancer, wherein the pharmaceutical composition induces an anticancer effect with respect to cancer by co-administering loperamide as an anticancer supplement with a proteasome inhibitor such as carfilzomib, MLN9708, epoxomicin, MG132, curcumin, or celastrol, as well as bortezomib, wherein the proteasome inhibitor is an effective treating agent when it is used at a high concentration to treat a blood cancer patient but has no anticancer effect in solid cancers.

BACKGROUND ART

The ubiquitin-proteasome system is a signaling mechanism that decomposes proteins to maintain cellular homeostasis and controls cell survival. Ubiquitin is a protein in vivo that conjugates and thus marks a condemned protein for degradation, and a proteasome is an enzyme that actually decomposes a protein.

When ubiquitin tags the condemned protein as a label, a proteasome recognizes the label and decomposes the protein. Then, ubiquitin is cleaved off the protein and repeats the same role. However, the protein decomposed by the ubiquitin-proteasome system is degraded into small peptides or amino acids and are recycled in synthesis of another protein.

The ubiquitin-proteasome system is also involved in a cell division process and an immune system that decomposes and disrupts an external antigen, and damages on the proteasome system are deemed as pathogenesis of neurodegenerative diseases such as Huntington diseases that occur when undegraded proteins accumulate in neurons. In this regard, since the proteasome system plays a vital role in a protein decomposition process, enlightenment on the structure or role of the system increases attention in the development of treating agents for various diseases.

In terms of cancer, the ubiquitin-proteasome system decomposes intercellular proteins such as Bax or Noxa that induce apoptosis and thus, the cancer cells may continue its proliferation. Thus, a drug that inhibits a proteasome is expected to promote apoptosis of cancer cells, and, in practice, bortezomib, for the first, and carfilzomib, for the second, have been approved by FDA as proteasome inhibitors.

Bortezomib (N-(2-pyrazine)carbonyl-L-phenylalanine-L-leucine boronic acid; available as Velcade™ from Millennuim Pharmaceuticals) is 26S proteasome inhibitor that is approved to be used in the treatment of various neoplastic diseases, particularly, in the treatment of relapsed multiple myeloma and mantle cell lymphoma.

The bortezomib has been reported that a boron atom in the bortezomib binds to a catalyst site, and this suppresses proteasome activities and decreases decomposition of a pro-apoptotic factor, which results in promotion of apoptosis of cells.

Korean Patent Publication No. 2007-7027765 discloses a method and a composition using a proteasome inhibitor for treatment and management of cancer and other diseases, and the same publication also discloses bortezomib exhibiting an anticancer effect on multiple myeloma and lymphoma, whereas an anticancer effect of the bortezomib on leukemia or solid cancers has not been testified.

DETAILED DESCRIPTION OF THE INVENTIVE CONCEPT

Technical Problem

In order to resolve the conventional problems, the present invention has been completed by confirming excellent anticancer effects since loperamide enhances an anticancer effect of a proteasome inhibitor and the cell death of cancer cells is effectively induced in solid cancers, as well as in blood cancers when at least one selected from bortezomib, carfilzomib, MLN9708, epoxomicin, MG132, curcumin, or celastrol, which are various proteasome inhibitors, is co-administered with loperamide that has been used as an antidiarrheal agent.

Therefore, the purpose of the present invention is to provide a co-administerable drug that reduces side effects of a proteasome inhibitor by allowing a proteasome inhibitor to be used at a low concentration in a blood cancer patient, can be used in treatment of various types of blood cancer, and, particularly, effectively induces cancer cell death in solid cancer that has not exhibited an anticancer effect to a proteasome inhibitor such as bortezomib.

Technical Solution

According to an aspect of the present invention, there is provided an anticancer supplement containing loperamide as an active ingredient.

Loperamide may reduce the resistance of a proteasome inhibitor as an anticancer agent.

Loperamide may be an anticancer supplement with respect to a cancer selected from the group consisting of solid cancer and blood cancer.

The proteasome inhibitor may be selected from the group consisting of bortezomib, carfilzomib, MLN9708, epoxomicin, MG132, curcumin, and celastrol.

The solid cancer may be selected from the group consisting of cervical cancer, kidney cancer, brain tumor, breast cancer, and colon cancer.

The blood cancer may be selected from the group consisting of leukemia, myeloma, and malignant lymphoma.

According to another aspect of the inventive concept, there is provided a pharmaceutical composition for preventing or treating cancer, and the pharmaceutical composition contains a proteasome inhibitor and loperamide as active ingredients.

The pharmaceutical composition may include the proteasome inhibitor ranging from about 1 wt % to about 50 wt % and the loperamide ranging from about 50 wt % to about 99 wt %.

The proteasome inhibitor may be selected from the group consisting of bortezomib, carfilzomib, MLN9708, epoxomicin, MG132, curcumin, and celastrol.

The cancer may be selected from the group consisting of solid cancer and blood cancer.

The solid cancer may be selected from the group consisting of cervical cancer, kidney cancer, brain tumor, breast cancer, and colon cancer.

The blood cancer may be selected from the group consisting of leukemia, myeloma, and malignant lymphoma.

According to another aspect of the inventive concept, there is provided a method of increasing cancer cell death by co-administering a proteasome inhibitor and loperamide to cancer cells.

Advantageous Effects

When a solid cancer cell was treated with a proteasome inhibitor such as bortezomib, carfilzomib, MLN9708, epoxomicin, MG132, curcumin, or celastrol and loperamide alone, cancer cell death was not induced, but when the proteasome inhibitor and loperamide were used together, cancer cell death was effectively induced. Also, multiple myeloma cancer cells have only exhibited an anticancer effect to a proteasome inhibitor of a high concentration, but when the proteasome inhibitor is co-administered with loperamide, effective cancer cell death was confirmed in the multiple myeloma cancer cells even with a low concentration of the proteasome inhibitor.

However, since co-administration of the proteasome inhibitor and loperamide does not induce cell death of normal cells, a composition including both the proteasome inhibitor and loperamide or co-administration of the proteasome inhibitor and loperamide is safe to normal cells, reduce side effects caused by the proteasome inhibitor of a high concentration, and may enhance an anticancer effect with respect to blood cancer cells and solid cancer cells.

BEST MODE

According to an embodiment of the present invention, provided is an anticancer supplement containing loperamide as an active ingredient.

Loperamide may reduce the resistance of a proteasome inhibitor as an anticancer agent.

Loperamide may be an anticancer supplement related to a cancer selected from the group consisting of solid cancer and blood cancer.

Figure 1:
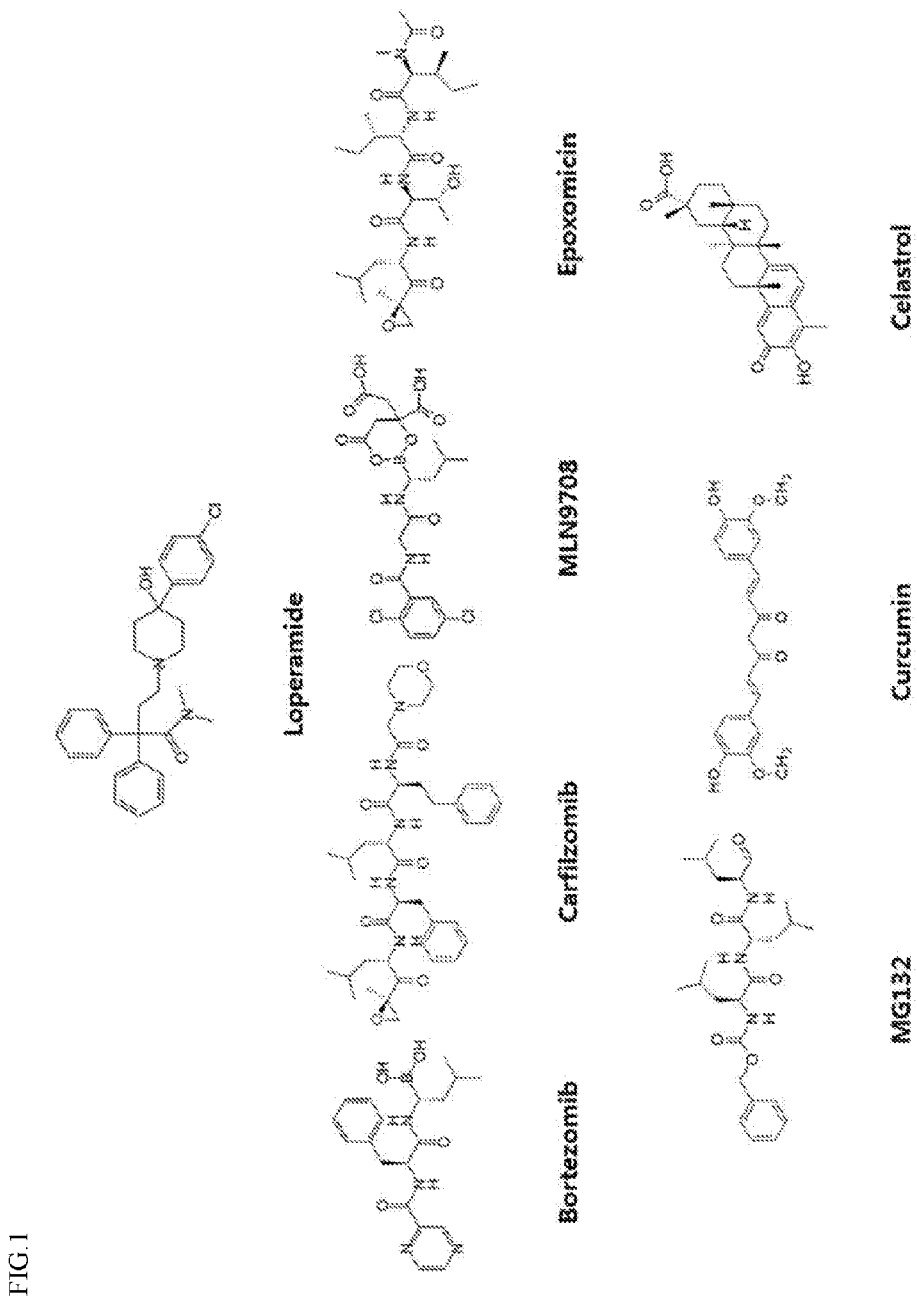
FIG. 1 shows a type and a chemical formula of each of loperamide and a proteasome inhibitor that are co-administered, according to the present invention.

The proteasome inhibitor may be selected from the group consisting of bortezomib, carfilzomib, MLN9708, epoxomicin, MG132, curcumin, and celastrol that are represented by formulae in FIG. 1.

The solid cancer may be selected from the group consisting of cervical cancer, kidney cancer, brain tumor, breast cancer, and colon cancer.

The blood cancer may be selected from the group consisting of leukemia, myeloma, and malignant lymphoma.

According to another embodiment of the present invention, provided is a pharmaceutical composition for preventing or treating cancer, and the pharmaceutical composition contains a proteasome inhibitor and loperamide as active ingredients.

The pharmaceutical composition may include the proteasome inhibitor ranging from about 1 wt % to about 50 wt % and the loperamide ranging from about 50 wt % to about 99 wt %.

The proteasome inhibitor may be selected from the group consisting of bortezomib, carfilzomib, MLN9708, epoxomicin, MG132, curcumin, and celastrol that are represented by formulae in FIG. 1.

The cancer may be selected from the group consisting of solid cancer and blood cancer.

The solid cancer may be selected from the group consisting of cervical cancer, kidney cancer, brain tumor, breast cancer, and colon cancer.

The blood cancer may be selected from the group consisting of leukemia, myeloma, and malignant lymphoma.

According to another embodiment of the present invention, a proteasome inhibitor and loperamide may be co-administered.

Here, when the proteasome inhibitor is contained in the pharmaceutical composition according to the present invention at an excessive amount beyond the range above, problems such as acute onset of symptomatic hypotension and thrombocytopenia may occur; but when contained at a small amount, the pharmaceutical effect may be insufficient.

Also, when the loperamide is contained in the pharmaceutical composition according to the present invention at an excessive amount beyond the range above, problems such as constipation, abdominal distension, or intestinal obstruction may occur; but when contained at a small amount, the pharmaceutical effect may be insufficient.

The pharmaceutical composition according to the present invention may further include suitable a carrier, an excipient, or a diluent that are generally used in manufacture of a pharmaceutical composition.

Examples of the carrier, excipient, or diluents that may be used in the present invention may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, or mineral oil, and the like.

The pharmaceutical composition according to the present invention may be formulated in the form of powders, granules, tablets, capsules, suspensions, emulsions, syrups, oral formulations such as aerosols, external applications, suppositories, and sterilized injectable solutions according to the respective method generally used in the art.

In the formulation of the pharmaceutical composition is formulated, fillers, extenders, binders, wetting agents, disintegrating agents, diluents such as surfactants, or excipients that are generally used in the art may be used. Examples of a solid formulation for oral administration may include tablets, pills, powders, granules, and capsules, and the solid formulation is prepared by mixing the compound with at least one excipient, for example, starch, calcium carbonate, sucrose, or lactose, and gelatin.

Also, lubricants such as magnesium stearate or talc in addition to simple excipients are used. Examples of a liquid formulation for oral administration may include suspensions, solutions, emulsions, and syrups, and various excipients, for example, wetting agents, sweeteners, aromatics, and preservatives may be included in addition to simple diluents such as water or liquid paraffin.

A dose of administration of the pharmaceutical composition according to the present invention may vary depending on age, sex, or body weight of a patient, and the proteasome inhibitor may be administered ranging from 1.0 mg/m$^2$/day to 1.3 mg/m$^2$/day, and loperamide may be administered ranging from 2 mg/day to 6 mg/day, twice a week for 1 to 4 weeks.

Also, the dose of administration may be increased or decreased depending on an administration route, a degree of disease, sex, body weight, or age. Therefore, the dose of administration does not limit the scope of the present invention in any aspect.

Also, the proteasome inhibitor and loperamide included in the pharmaceutical composition according to the present invention have been already prescribed for other medical use and thus are materials secured with safety.

The composition of the present invention may be topically applied to oral administration or parenteral administration, for example, intravenous, subcutaneous, intraperitoneal, and ranges of the dose of administration may vary depending on body weight, age, sex, health status, diet, administration time, administration method, excretion rate, and severity of disease of a patient.

The composition of the present invention may be used alone for prevention or treatment of solid cancer or may be combined with operation, hormone treatment, and methods that use biological reaction controlling agents.

MODE OF THE INVENTIVE CONCEPT

Hereinafter, one or more embodiments of the present invention will be described in detail with reference to the following examples. However, these examples are not intended to limit the scope of the present invention.

The examples are provided herein for experimental examples applied to each of the embodiment according to the present invention.

Experimental Example 1 Cell Culture

Strains of cervical cancer cell (HeLa), kidney cancer cell (Caki-1), brain tumor cell (T98G), breast cancer cell (MDA-MB 435S), and colon cancer cell (DLD-1), multiple myeloma cell (RPMI-8226), and a strain of normal breast epithelial cell (MCF-10A) were available from ATCC (American Type Culture Collection, USA). The strains of cervical cancer cell (HeLa), kidney cancer cell (Caki-1), brain tumor cell (T98G), breast cancer cell (MDA-MB 435S), and colon cancer cell (DLD-1) were cultured by using a DMEM medium including 10% fetal bovine serum (FBS), 2 mM of L-glutamin, 100 i.u./ml of penicillin, and 10 mg/ml of streptomycin for the culture and maintenance; multiple myeloma cell (RPMI-8226) was cultured by using a RPMI1640 medium including 10% FBS, 100 i.u./ml of penicillin, and 10 mg/ml of streptomycin; and the strain of normal breast epithelial cell (MCF-10A) was cultured by using a mammary epithelial growth medium (MEGM) including a bovine pituitary extract, insulin, human epidermal growth factor, hydrocortisone, and antibiotics, and the culture conditions included 37° C. and 5% $CO_2$ in an incubator.

Experimental Example 2 Chemicals

Bortezomib, carfilzomib, and MLN9708, as a proteasome inhibitor, were available from Selleckchem (Houston, Tex., USA), and epoxomicin, MG132, curcumin, celastrol, and loperamide were available from Sigma Chemical Corporation.

Calcein acetoxyl methylester (calcein-AM) and ethidium homodimer-1 were available from Invitrogen (Carlsbad, Calif.).

Experimental Example 3 Measurement of Cell Viability

In order to measure cell viability of various cancer cell strains and normal breast epithelial cells with respect to single or combined treatment of a proteasome inhibitor and loperamide, each of the strains was inoculated so that the number of cells per well was HeLa $1\times10^4$, Caki-1 $0.75\times10^4$, T98G $0.5\times10^4$, MDA-MB 435S $0.75\times10^4$, DLD-1 $1.5\times10^4$, and RPMI-8226 $5\times10^4$ in a 96-well plate, and, in the case of the MCF-10A cells, the cells were inoculated so that the number of cells per well was $6\times10^4$ in a 24-well plate. The proteasome inhibitor of various concentrations and loperamide of 0 to 40 μM were each used alone or as a combination for treating the strains or cells for 24 hours. Then, the cells were stained by using 2 μM calcein-AM and 4 μM ethidium homodimer-1, and cell viability was measured by using a fluorescent microscope (Axiovert 200M, available from Carl Zeiss, Jena, Germany).

Experimental Example 4 Isobologram Analysis

In order to confirm an effect and to determine an effective concentration of each of compounds when HeLa, Caki-1, T98G, MDA-MB 435S, and DLD-1 were each treated with the proteasome inhibitor and loperamide alone or as a combination, isobologram analysis was performed. An interaction between the proteasome inhibitor and loperamide was quantified by measuring a combination index (CI) in accordance with typical isobologram.

An isobologram quantification method is $CI=(D)_1/(Dx)_1+(D)_2/(Dx)_2$, where $(Dx)_1$ and $(Dx)_2$ each represent an individual amount of each of the proteasome inhibitor and loperamide that is required to exhibit the effect, and $(D)_1$ and $(D)_2$ each represent an amount for exhibiting the same effect when the proteasome inhibitor and loperamide are combined. Through the analysis, a combination effect of the two drugs was represented by CI<1, indicating an synergetic effect; CI=1, indicating an additive effect; or CI>1, indicating an antagonistic effect.

Experimental Example 5 Statistic Analysis

All data of the results of experiment repeated at least 3 times were shown as ±standard deviation (SD), and cell viability difference between a drug-treated group and a control group was evaluated by t-test.

The results of various groups were analyzed by one-way ANOVA according to the Bonferroni multiple comparison test, and P<0.05 was considered as a significant value.

Figure 2:
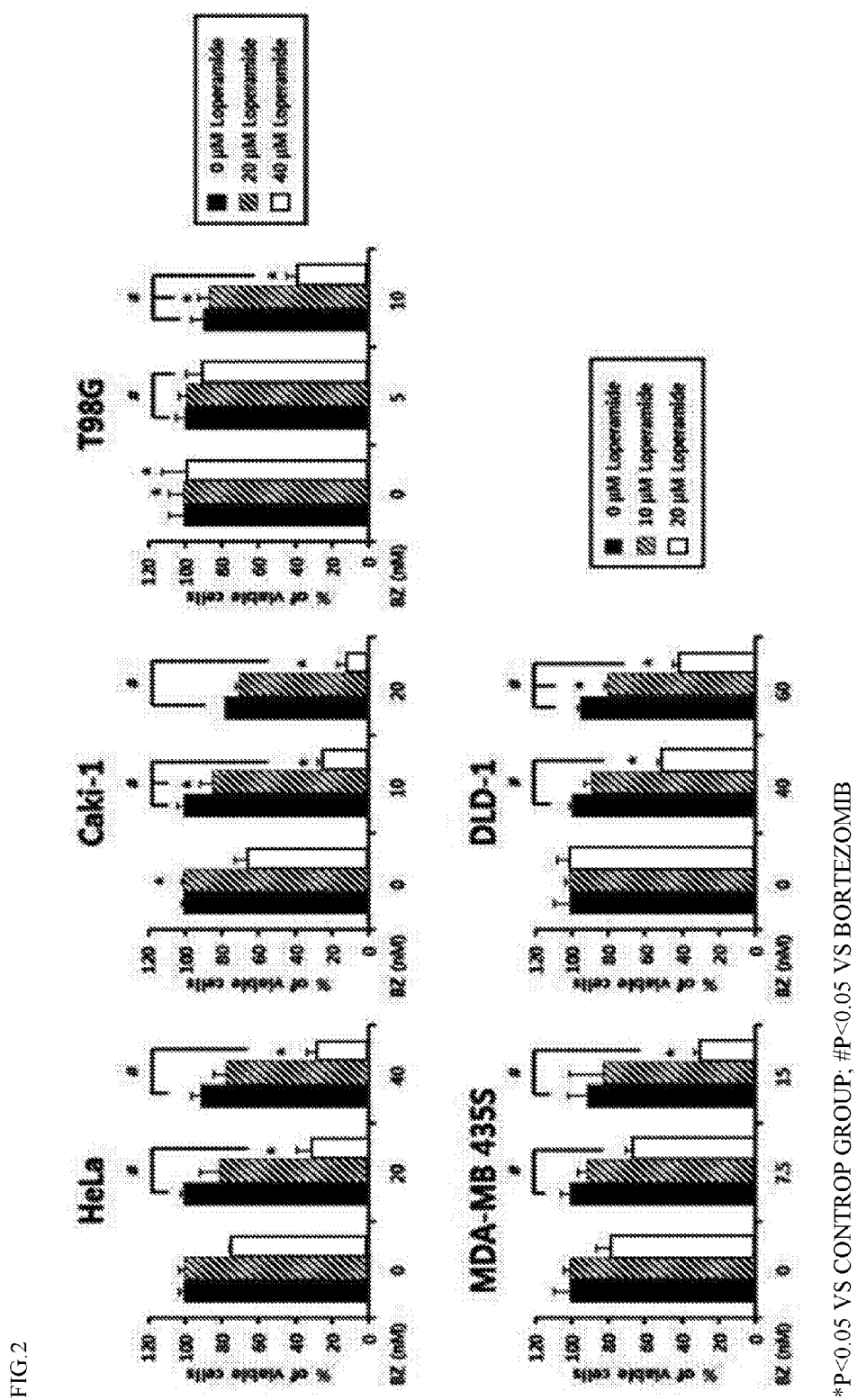
FIG. 2 shows the results of cell viability analysis to confirm the anticancer effect produced by co-administration of bortezomib (BZ) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 3:
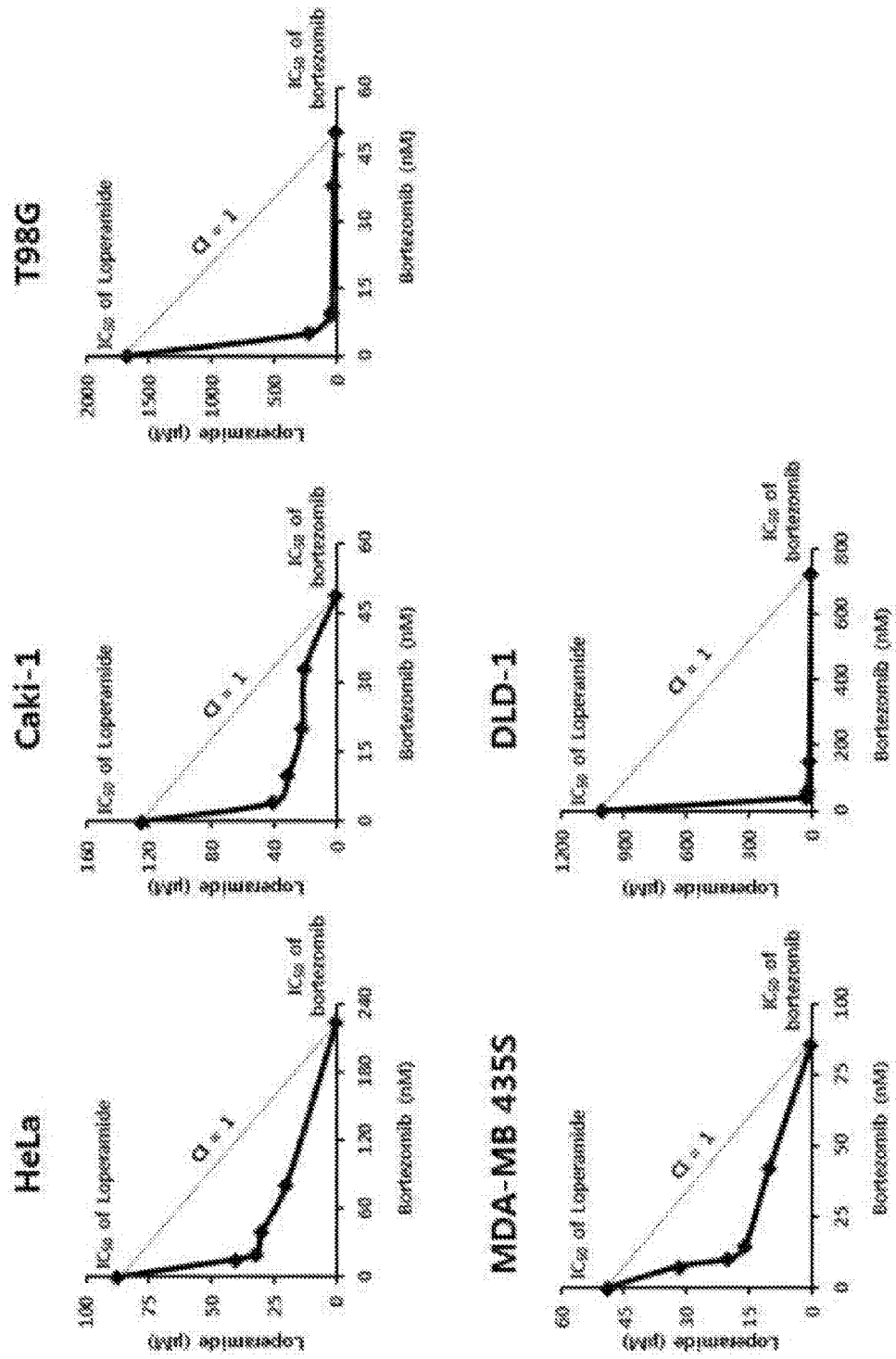
FIG. 3 shows the results of isobologram analysis to confirm the anticancer effect produced by co-administration of bortezomib and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 1 Confirmation of Anticancer Effect Following to Combined Administration of Bortezomib and Loperamide on Solid Cancer Cells HeLa, Caki-1, T98G, MDA-MB 435S, and DLD-1 cells were each single- or combination-treated with loperamide and bortezomib (BZ) at concentrations shown in FIG. 2 for 24 hours, and the cell viability was measured by using calcein-AM and ethidium homodimer-1. Then, isobologram analysis was performed thereon as shown in FIG. 3.

As the results shown in Table 1, the cell viability of the HeLa cells treated with bortezomib alone at a concentration of 40 nM decreased about 10%, and the cell viability at a concentration of 40 μM decreased about 25% when treated with loperamide alone; whereas, when treated with a combination of bortezomib and loperamide, cancer cell death increased drug concentration-dependently and significantly, compared to the case when the HeLa cells were treated with each of the bortezomib and loperamide alone. Also, as shown in Table 2, the viability of the Caki-1 cells treated with bortezomib alone at a concentration of 20 nM decreased about 22%, and the cell viability at a concentration of 40 μM decreased about 35% when treated with loperamide alone; whereas, when treated with a combination of bortezomib and loperamide, cancer cell death increased drug concentration-dependently and significantly, compared to the case when the Caki-1 cells were treated with each of the bortezomib and loperamide alone.

As shown in Table 3, T98G cells were a slightly sensitive to bortezomib compared to those of other cancer cells and did not exhibit significant cancer cell toxicity with respect to loperamide up to a concentration of 20 μM, but when treated with a combination of bortezomib and loperamide, cancer cell death increased drug concentration-dependently and significantly, compared to the case when the T98G cells were treated with each of the bortezomib and loperamide alone.

As shown in Table 4, the MDA-MB 435S cells treated with bortezomib alone did not induce cancer cell toxicity up to 15 nM, cancer cell viability at a concentration of 20 μM decreased about 25% when treated with loperamide alone; whereas, when treated with a combination of bortezomib and loperamide, cancer cell death increased drug concentration-dependently and significantly, compared to the case when the MDA-MB 435S cells were treated with each of the bortezomib and loperamide alone.

As shown in Table 5, DLD-1 cells exhibited more resistance to bortezomib-single treatment and loperamide-single treatment compared to other cancer cells, but when treated with a combination of bortezomib and loperamide, cancer cell death increased drug concentration-dependently and significantly, compared to the case when the DLD-1 cells were treated with each of the bortezomib and loperamide alone.

Also, in the isobologram analysis shown in FIG. 3, effective cancer cell death was induced in all Hela, Caki-1, T98G, MDA-MB 435S, and DLD-1 cells when a combination of the bortezomib and loperamide was used in the treatment. In this regard, it may be confirmed that combined administration of bortezomib and loperamide overcame resistance to bortezomib and exhibited an improved anticancer effect on various solid cancer cells.

TABLE 1

| HeLa | | | |
|---|---|---|---|
| Loperamide | | Cell viability Bortezomib-added group | |
| concentration | Control group | 20 nM | 40 nM |
| 0 μM | 100 | 100 | 90.78 |
| 20 μM | 99.71 | 80.54 | 76.36 |
| 40 μM | 75.09 | 30.88 | 28.44 |

TABLE 2

| Caki-1 | | | |
|---|---|---|---|
| Loperamide | | Cell viability Bortezomib-added group | |
| concentration | Control group | 10 nM | 20 nM |
| 0 μM | 100 | 100 | 77.95 |
| 20 μM | 100 | 84.68 | 69.76 |
| 40 μM | 65.09 | 25.95 | 12.43 |

TABLE 3

| T98G | | | |
|---|---|---|---|
| Loperamide | Control | Cell viability Bortezomib-added group | |
| concentration | group | 5 nM | 10 nM |
| 0 μM | 100 | 99.71 | 89.65 |
| 10 μM | 100 | 98.54 | 90.45 |
| 20 μM | 99 | 86.52 | 38.38 |

TABLE 4

| MDA-MB 435S | | | |
|---|---|---|---|
| Loperamide | Control | Cell viability Bortezomib-added group | |
| concentration | group | 7.5 nM | 15 nM |
| 0 μM | 100 | 100 | 91.04 |
| 10 μM | 100 | 91.45 | 82.27 |
| 20 μM | 77.95 | 66.70 | 30.05 |

TABLE 5

| DLD-1 | | | |
|---|---|---|---|
| Loperamide | Control | Cell viability Bortezomib-added group | |
| concentration | group | 40 nM | 60 nM |
| 0 μM | 100 | 99.70 | 94.95 |
| 10 μM | 100 | 88.13 | 79.52 |
| 20 μM | 100 | 50.44 | 41.24 |

Figure 4:
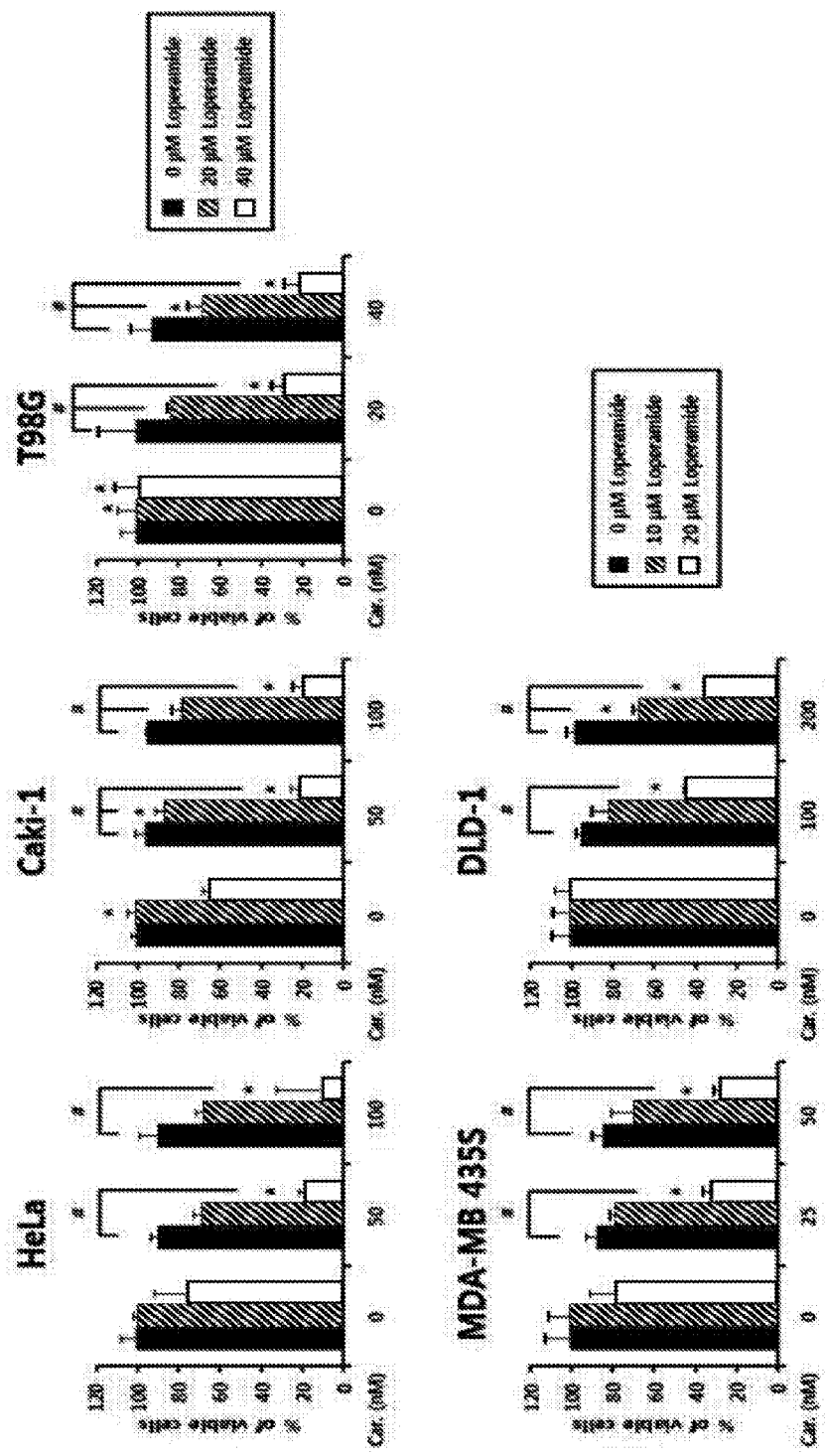
FIG. 4 shows the results of cell viability analysis to confirm the anticancer effect produced by co-administration of carfilzomib (Car.) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 5:
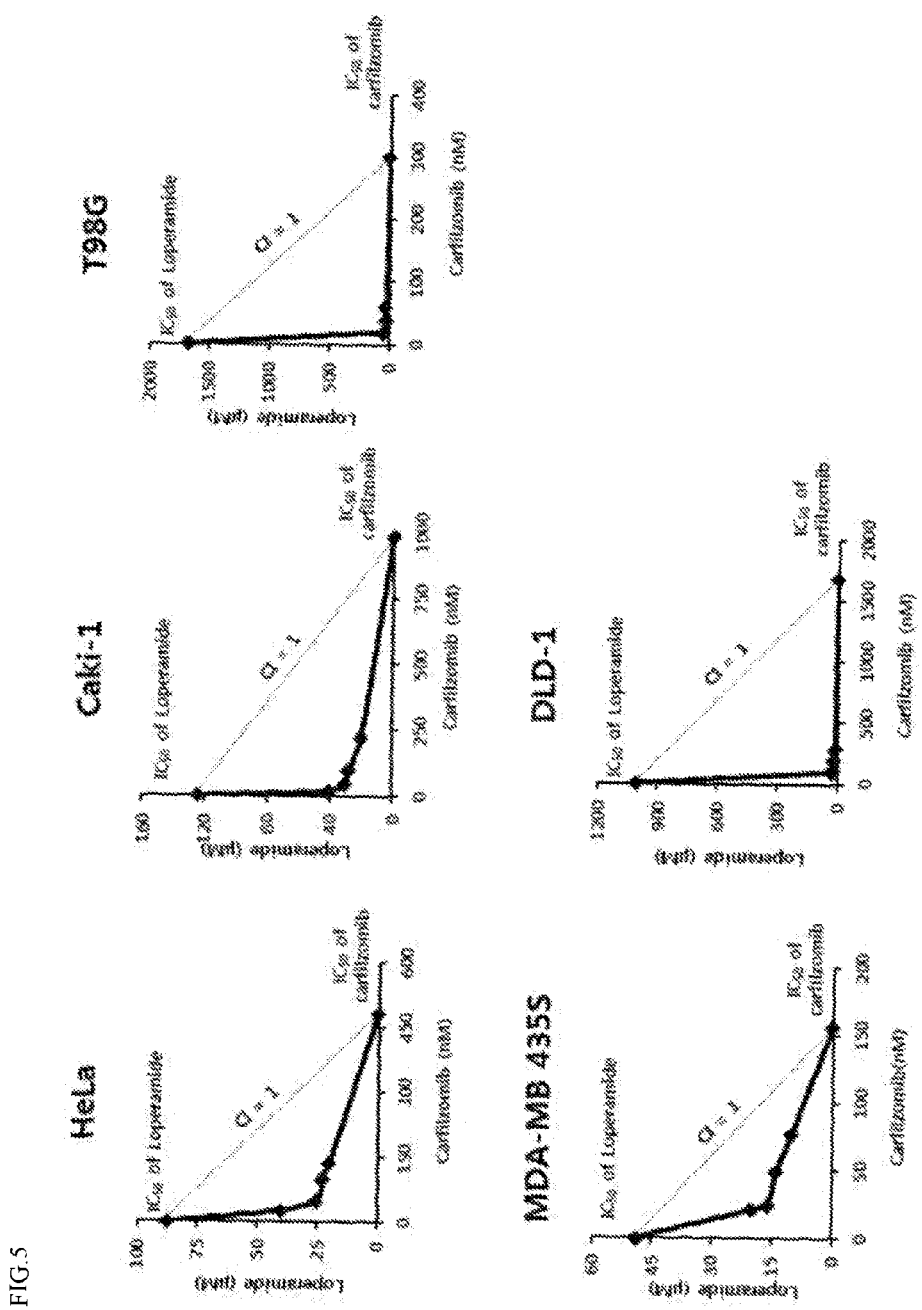
FIG. 5 shows the results of isobologram analysis to confirm the anticancer effect produced by co-administration of carfilzomib and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 2 Confirmation of Anticancer Effect Following to Combined Administration of Carfilzomib and Loperamide on Solid Cancer Cells HeLa, Caki-1, T98G, MDA-MB 435S, and DLD-1 cells were each single- or combination-treated with carfilzomib (Car.) and loperamide at concentrations shown in FIG. 4 for 24 hours, and the cell viability was measured by using calcein-AM and ethidium homodimer-1. Then, isobologram analysis was performed thereon as shown in FIG. 5.

As the results shown in Table 6, cell viability of the HeLa cells treated with carfilzomib alone at a concentration of 100 nM decreased about 10%, and the cell viability at a concentration of 40 μM decreased about 25% when treated with loperamide alone; when treated with a combination of carfilzomib and loperamide, cancer cell death increased drug concentration-dependently and significantly, compared to the case when the HeLa cells were treated with each of the carfilzomib and loperamide alone. Also, as shown in Table 7, cell viability of the Caki-1 cells treated with carfilzomib alone up to a concentration of 100 nM decreased about 5%, and the cancer cell viability at a concentration of 40 μM decreased about 35% when treated with loperamide alone; whereas, when treated with a combination of carfilzomib and loperamide, cancer cell death increased drug concentration-dependently and significantly, compared to the case when the Caki-1 cells were treated with each of the carfilzomib and loperamide alone.

As shown in Table 8, T98G cell was a slightly sensitive to carfilzomib compared to those of other cancer cells and did not exhibit significant cancer cell toxicity with respect to loperamide up to a concentration of 20 μM, but when treated with a combination of carfilzomib and loperamide, cancer cell death increased drug concentration-dependently and significantly, compared to the case when the T98G cells were treated with each of the carfilzomib and loperamide alone.

As shown in Table 9, cell viability of the MDA-MB 435S cells treated with carfilzomib alone at a concentration of 50 nM decreased about 15%, and the cell viability at a concentration of 20 μM decreased about 22% when treated with loperamide alone; when treated with a combination of carfilzomib and loperamide, cancer cell death increased drug concentration-dependently and significantly, compared to the case when the MDA-MB 435S cells were treated with each of the carfilzomib and loperamide alone.

As shown in Table 10, DLD-1 cells exhibited more resistance to carfilzomib-single treatment and loperamide-single treatment compared to other cancer cells, but when treated with a combination of carfilzomib and loperamide, cell death increased drug concentration-dependently and significantly, compared to the case when the DLD-1 cells were treated with each of the carfilzomib and loperamide alone.

In the isobologram analysis results shown in FIG. 5, it may be confirmed that effective cancer cell death was induced in all the HeLa, Caki-1, T98G, MDA-MB 435S, and DLD-1 cells when a combination of the carfilzomib and loperamide was used in the treatment. In this regard, it may be confirmed that combined administration of carfilzomib and loperamide overcame resistance to carfilzomib and exhibited an improved anticancer effect on various solid cancer cells.

TABLE 6

HeLa

| Loperamide concentration | Control group | Cell viability Carfilzomib-added group | |
|---|---|---|---|
| | | 50 nM | 100 nM |
| 0 μM | 100 | 89.97 | 89.80 |
| 20 μM | 99.81 | 68.50 | 67.21 |
| 40 μM | 75.09 | 19.09 | 10.82 |

TABLE 7

Caki-1

| Loperamide concentration | Control group | Cell viability Carfilzomib-added group | |
|---|---|---|---|
| | | 50 nM | 100 nM |
| 0 μM | 100 | 95.58 | 95.17 |
| 20 μM | 100 | 86.41 | 78.47 |
| 40 μM | 65.09 | 21.53 | 19.78 |

TABLE 8

T98G

| Loperamide concentration | Control group | Cell viability Carfilzomib-added group | |
|---|---|---|---|
| | | 20 nM | 40 nM |
| 0 μM | 100 | 100 | 93.00 |
| 10 μM | 100 | 86.36 | 29.41 |
| 20 μM | 99 | 67.26 | 21.55 |

TABLE 9

MDA-MB 435S

| Loperamide concentration | Control group | Cell viability Carfilzomib-added group | |
|---|---|---|---|
| | | 25 nM | 50 nM |
| 0 μM | 100 | 87.11 | 84.42 |
| 10 μM | 100 | 78.23 | 69.10 |
| 20 μM | 77.95 | 32.91 | 27.95 |

TABLE 10

DLD-1

| Loperamide concentration | Control group | Cell viability Carfilzomib-added group | |
|---|---|---|---|
| | | 100 nM | 200 nM |
| 0 μM | 100 | 98.21 | 94.65 |
| 10 μM | 100 | 81.30 | 66.46 |
| 20 μM | 100 | 44.51 | 35.90 |

Figure 6:
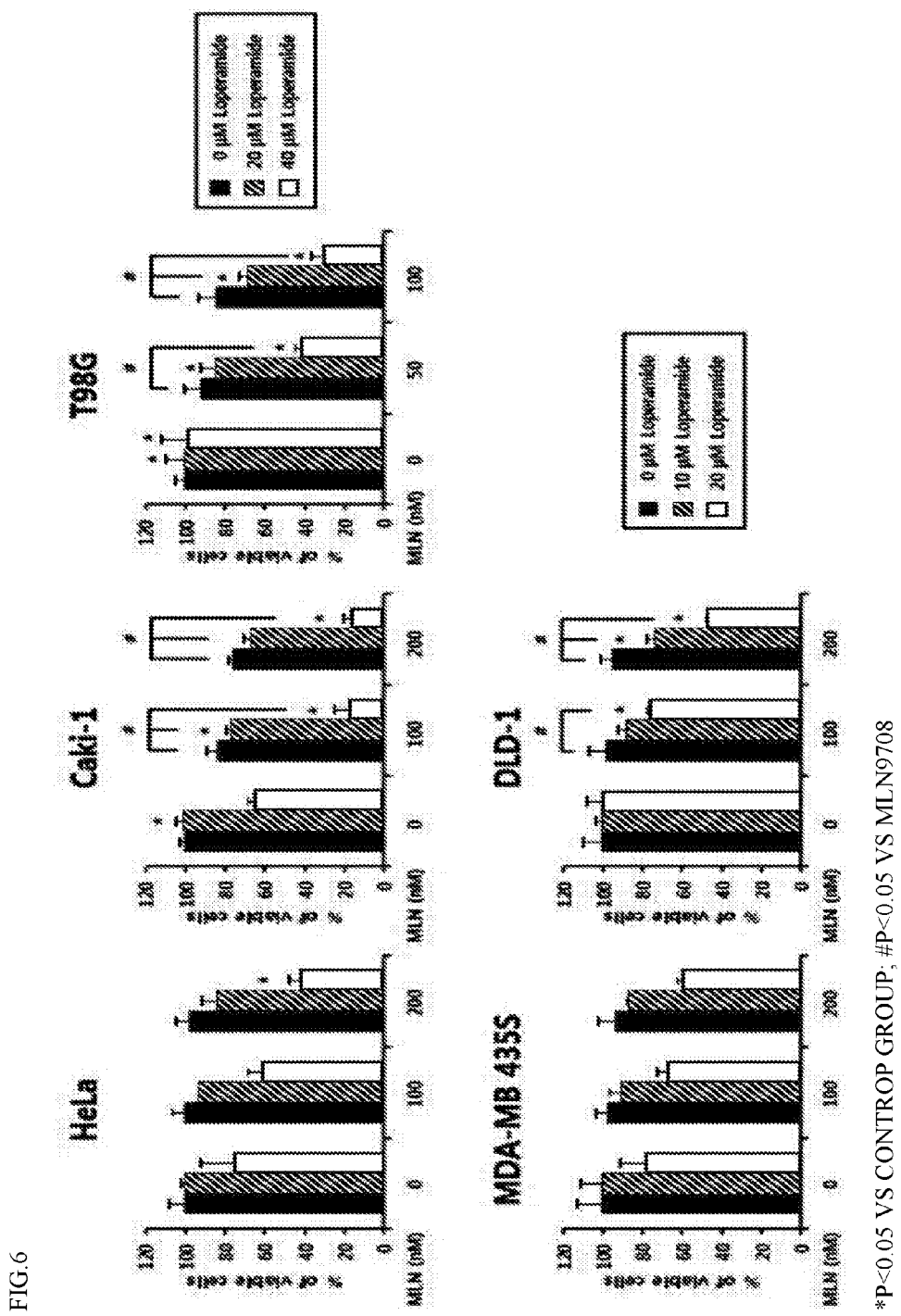
FIG. 6 shows the results of cell viability analysis to confirm the anticancer effect produced by co-administration of MLN9708 (MLN) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 7:
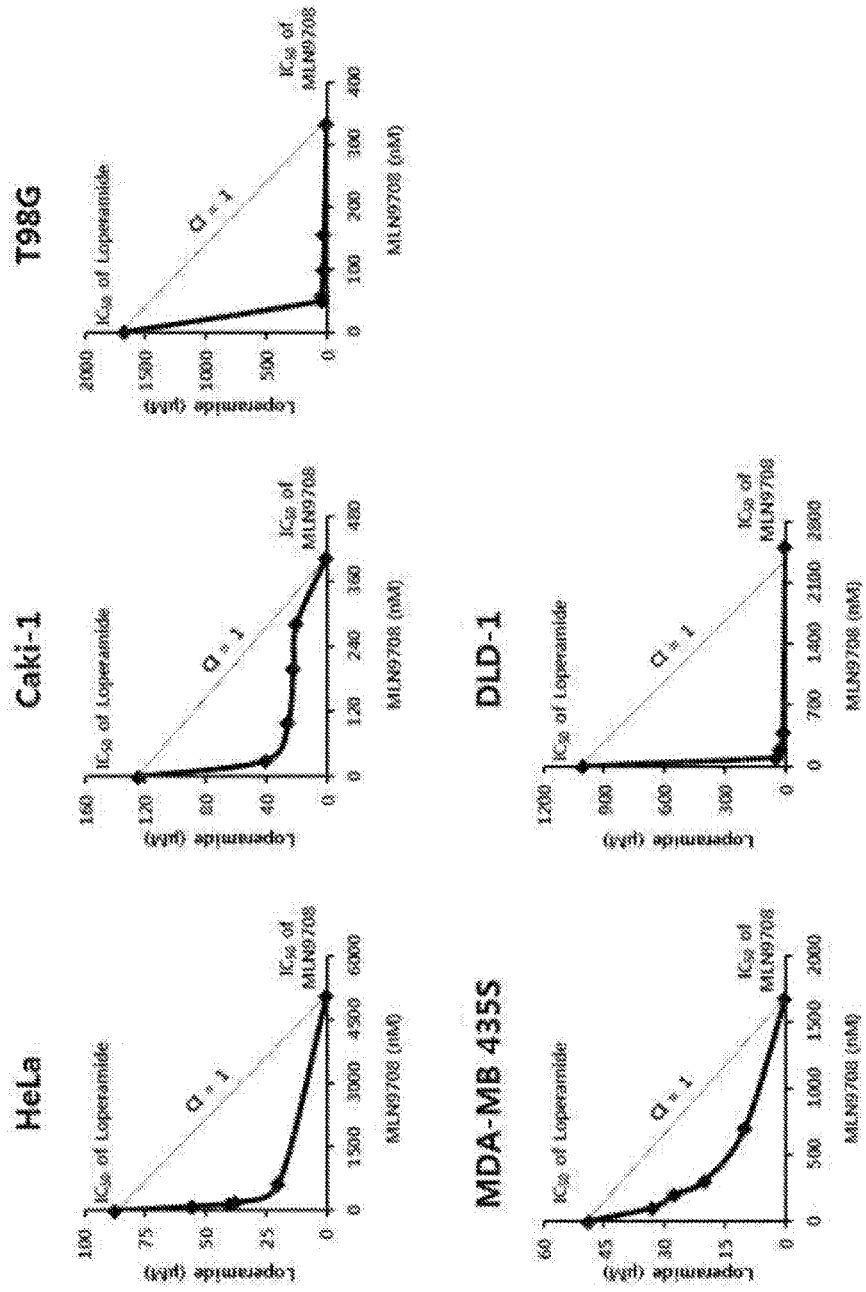
FIG. 7 shows the results of isobologram analysis to confirm the anticancer effect produced by co-administration of MLN9708 and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 3 Confirmation of Anticancer Effect Following to Combined Administration of MLN9708 and Loperamide on Solid Cancer Cells HeLa, Caki-1, T98G, MBA-MB 435S, and DLD-1 cells were each single- or combination-treated with MLN9708 (MLN) and loperamide at concentrations shown in FIG. 6 for 24 hours, and the cell viability was measured by using calcein-AM and ethidium homodimer-1. Then, isobologram analysis was performed thereon as shown in FIG. 7.

As the results of cell viability analysis shown in Table 11, the HeLa cells treated with MLN9708 alone did not exhibit cell toxicity up to a concentration of 200 nM, and the cell viability at a concentration of 40 μM decreased about 25% when treated with loperamide alone; whereas, when treated with a combination of MLN9708 and loperamide, cancer cell death increased drug concentration-dependently and significantly, compared to the case when the HeLa cells were treated with each of the MLN9708 and loperamide alone.

As shown in Table 12, cell viability of the Caki-1 cells treated with MLN9708 alone at a concentration of 200 nM decreased about 25%, and the cell viability at a concentration of 40 μM decreased about 35% when treated with loperamide alone; when treated with a combination of MLN9708 and loperamide, cancer cell death increased drug concentration-dependently and significantly, compared to the case when the Caki-1 cells were treated with each of the MLN9708 and loperamide alone. Also, referring to Table 13, the T98G cell was slightly sensitive to MLN9708 compared to those of other cancer cells and did not exhibit significant cancer cell toxicity with respect to loperamide up to a concentration of 20 μM, but when treated with a combination of MLN9708 and loperamide, cancer cell death increased drug concentration-dependently and significantly, compared to the case when the T98G cells were treated with each of the MLN9708 and loperamide alone.

Also, as shown in Table 14, cell viability of the MDA-MB 435S cells treated with MLN9708 alone at a concentration of 200 nM decreased about 10%, and the cancer cell viability at a concentration of 20 μM decreased about 25% when treated with loperamide alone; when treated with a combination of MLN9708 and loperamide, cancer cell death increased drug concentration-dependently and significantly, compared to the case when the MDA-MB 435S cells were treated with each of the MLN9708 and loperamide alone.

As shown in Table 15, DLD-1 cells exhibited more resistance to MLN9708-single treatment and loperamide-single treatment compared to other cancer cells, but when treated with a combination of MLN9708 and loperamide, cancer cell death increased drug concentration-dependently and significantly, compared to the case when the DLD-1 cells were treated with each of the MLN9708 and loperamide alone.

Also, in the isobologram analysis results shown in FIG. 7, it may be confirmed that effective cancer cell death was induced in all the HeLa, Caki-1, T98G, MDA-MB 435S, and DLD-1 cells when a combination of the MLN9708 and loperamide was used in the treatment. In this regard, it may be confirmed that combined administration of MLN9708 and loperamide overcame resistance to MLN9708 and exhibited an improved anticancer effect on various solid cancer cells.

TABLE 11

HeLa

| Loperamide concentration | Control group | Cell viability MLN9708-added group | |
|---|---|---|---|
| | | 100 nM | 200 nM |
| 0 μM | 100 | 100 | 97.75 |
| 20 μM | 99.71 | 93.04 | 83.87 |
| 40 μM | 75.09 | 60.81 | 42.08 |

TABLE 12

Caki-1

| Loperamide concentration | Control group | Cell viability MLN9708-added group | |
|---|---|---|---|
| | | 100 nM | 200 nM |
| 0 μM | 100 | 83.27 | 75.72 |
| 20 μM | 100 | 76.97 | 66.79 |
| 40 μM | 65.09 | 17.18 | 16.67 |

TABLE 13

T98G

| Loperamide concentration | Control group | Cell viability MLN9708-added group | |
|---|---|---|---|
| | | 50 nM | 100 nM |
| 0 μM | 100 | 91.98 | 84.65 |
| 10 μM | 100 | 84.16 | 40.92 |
| 20 μM | 99 | 68.07 | 29.90 |

TABLE 14

MDA-MB 435S

| Loperamide concentration | Control group | Cell viability MLN9708-added group | |
|---|---|---|---|
| | | 100 nM | 200 nM |
| 0 μM | 100 | 97.48 | 93.27 |
| 10 μM | 100 | 90.71 | 86.70 |
| 20 μM | 77.95 | 67.16 | 59.13 |

TABLE 15

DLD-1

| Loperamide concentration | Control group | Cell viability MLN9708-added group | |
|---|---|---|---|
| | | 100 nM | 200 nM |
| 0 μM | 100 | 98.21 | 95.25 |
| 10 μM | 100 | 87.83 | 73.29 |
| 20 μM | 100 | 76.55 | 46.88 |

Figure 8:
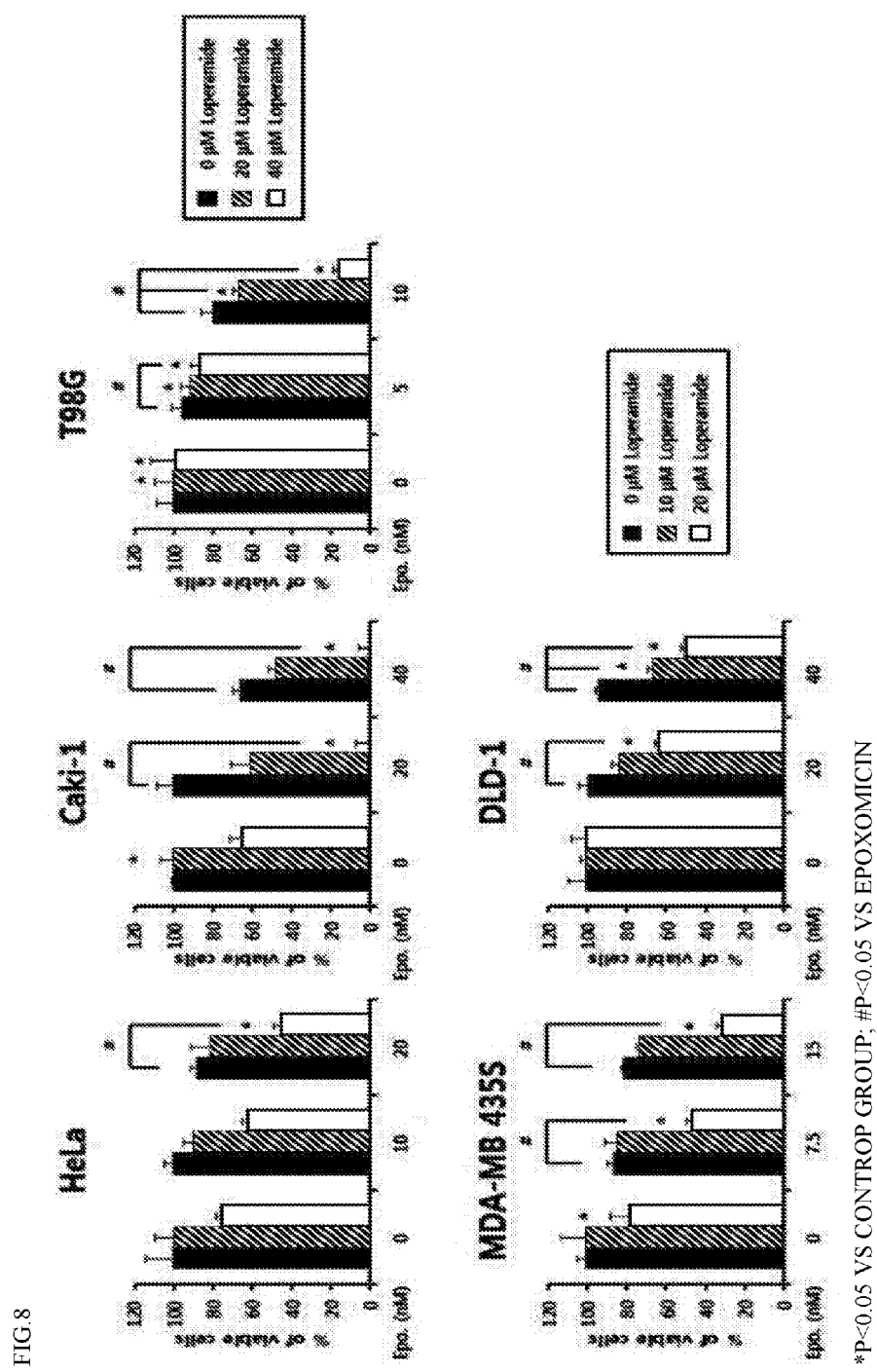
FIG. 8 shows the results of cell viability analysis to confirm the anticancer effect produced by co-administration of epoxomicin (Epo.) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 9:
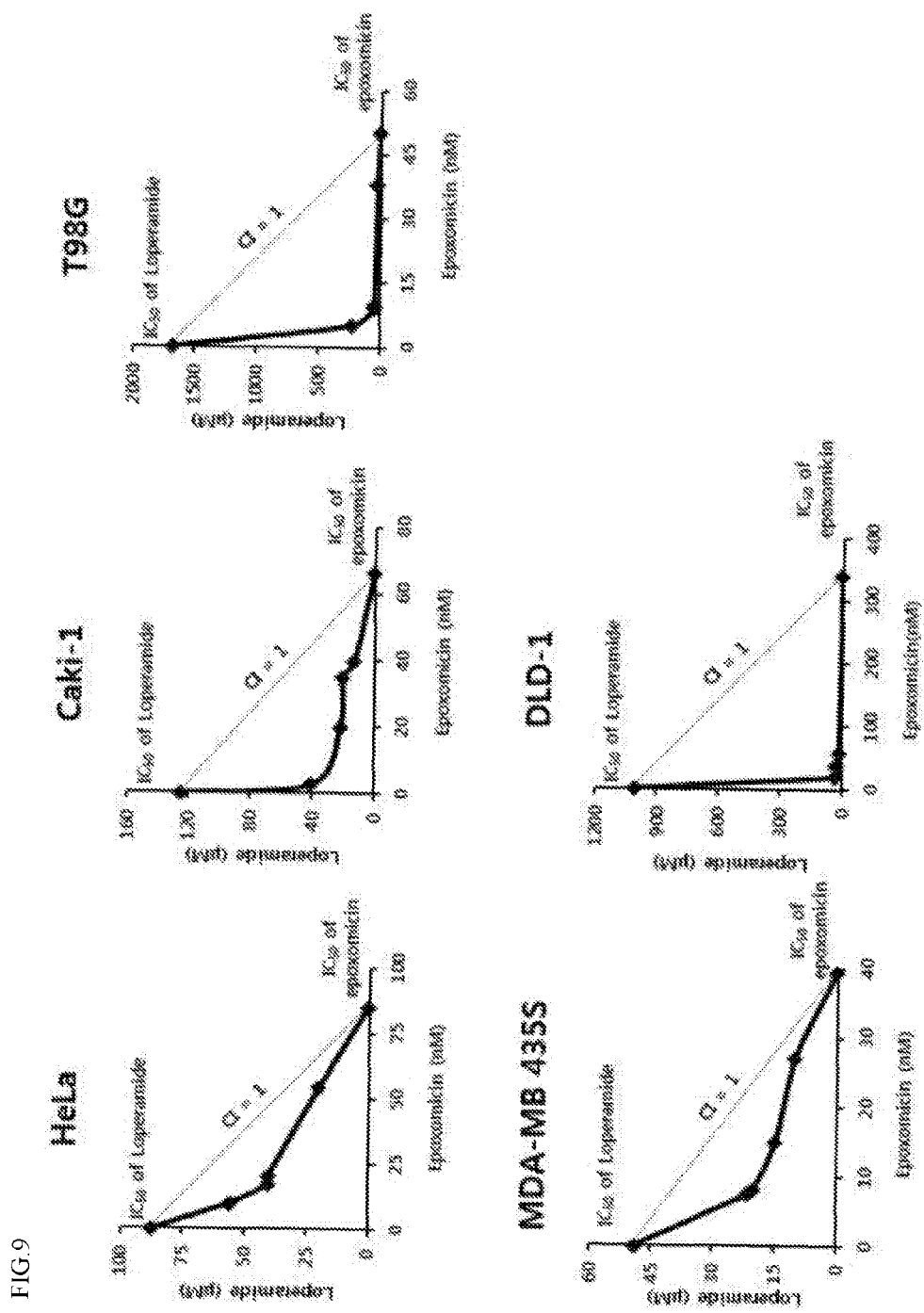
FIG. 9 shows the results of isobologram analysis to confirm the anticancer effect produced by co-administration of epoxomicin and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 4 Confirmation of Anticancer Effect Following to Combined Administration of Epoxomicin and Loperamide on Solid Cancer Cells HeLa, Caki-1, T98G, MDA-MB 435S, and DLD-1 cells were each single- or combination-treated with epoxomicin (Epo.) and loperamide at concentrations shown in FIG. 8 for 24 hours, and the cell viability was measured by using calcein-acetoxy methylether and ethidium homodimer-1. FIG. 9 shows the results of isobologram analysis with respect to the anticancer effect of co-administration of epoxomicin and loperamide.

As the results of cell viability analysis shown in Table 8, a cancer cell viability of the HeLa cells treated with epoxomicin alone at a concentration of 20 nM decreased about 12%, and the cancer cell viability at a concentration of 40 μM decreased about 25% when treated with loperamide alone; whereas, when treated with a combination of epoxomicin and loperamide, cancer cell death increased drug concentration-dependently and significantly, compared to the case when the HeLa cells were treated with each of the epoxomicin and loperamide alone.

Also, as shown in Table 17, cell viability of the Caki-1 cells treated with epoxomicin alone did not induce cancer cell toxicity up to 20 nM and decreased about 35% at a concentration of 40 nM, and the cancer cell viability at a concentration of 40 μM decreased about 35% when treated with loperamide alone; whereas, when treated with a combination of epoxomicin and loperamide, cancer cell death increased drug concentration-dependently and significantly, compared to the case when the Caki-1 cells were treated with each of the epoxomicin and loperamide alone.

As shown in Table 18, T98G cell was a slightly sensitive to epoxomicin compared to those of other cancer cells and did not exhibit significant cancer cell toxicity with respect to loperamide up to a concentration of 20 μM, but when treated with a combination of epoxomicin and loperamide, cancer cell death increased drug concentration-dependently and significantly, compared to the case when the T98G cells were treated with each of the epoxomicin and loperamide alone.

As shown in Table 19, cell viability of the MDA-MB 435S cells treated with epoxomicin alone at a concentration of 15 nM decreased about 18%, and the cancer cell viability at a concentration of 20 μM decreased about 25% when treated with loperamide alone; when treated with a combination of epoxomicin and loperamide, cancer cell death increased drug concentration-dependently and significantly, compared to the case when the MDA-MB 435S cells were treated with each of the epoxomicin and loperamide alone.

As shown in Table 20, DLD-1 cells exhibited more resistance to epoxomicin-single treatment and loperamide-single treatment compared to other cancer cells, but when treated with a combination of epoxomicin and loperamide, cancer cell death increased drug concentration-dependently and significantly, compared to the case when the DLD-1 cells were treated with each of the epoxomicin and loperamide alone.

Also, in the isobologram analysis results shown in FIG. 9, it may be confirmed that effective cancer cell death was induced in all the HeLa, Caki-1, T98G, MDA-MB 435S, and DLD-1 cells when a combination of the epoxomicin and loperamide was used in the treatment. In this regard, it may be confirmed that combined administration of epoxomicin and loperamide overcame resistance to epoxomicin and exhibited an improved anticancer effect in various solid cancer cells.

TABLE 16

HeLa

| Loperamide concentration | Control group | Cell viability Epoxomicin-added group | |
| --- | --- | --- | --- |
| | | 10 nM | 20 nM |
| 0 μM | 100 | 100 | 87.73 |
| 20 μM | 99.71 | 89.76 | 81.55 |
| 40 μM | 75.09 | 61.97 | 45.26 |

TABLE 17

Caki-1

| Loperamide concentration | Control group | Cell viability Epoxomicin-added group | |
| --- | --- | --- | --- |
| | | 20 nM | 40 nM |
| 0 μM | 100 | 100 | 66.45 |
| 20 μM | 100 | 60.99 | 47.62 |
| 40 μM | 65.09 | 0.65 | 0 |

TABLE 18

T98G

| Loperamide concentration | Control group | Cell viability Epoxomicin-added group | |
| --- | --- | --- | --- |
| | | 5 nM | 10 nM |
| 0 μM | 100 | 95.66 | 79.79 |
| 10 μM | 100 | 90.77 | 86.82 |
| 20 μM | 99 | 65.86 | 16.15 |

TABLE 19

MDA-MB 435S

| Loperamide concentration | Control group | Cell viability Epoxomicin-added group | |
| --- | --- | --- | --- |
| | | 7.5 nM | 15 nM |
| 0 μM | 100 | 86.50 | 81.52 |
| 10 μM | 100 | 84.52 | 72.69 |
| 20 μM | 77.95 | 46.39 | 31.58 |

TABLE 20

DLD-1

| Loperamide concentration | Control group | Cell viability Epoxomicin-added group | |
| --- | --- | --- | --- |
| | | 20 nM | 40 nM |
| 0 μM | 100 | 99.70 | 94.06 |
| 10 μM | 100 | 83.67 | 66.17 |
| 20 μM | 100 | 64.09 | 49.85 |

Figure 10:
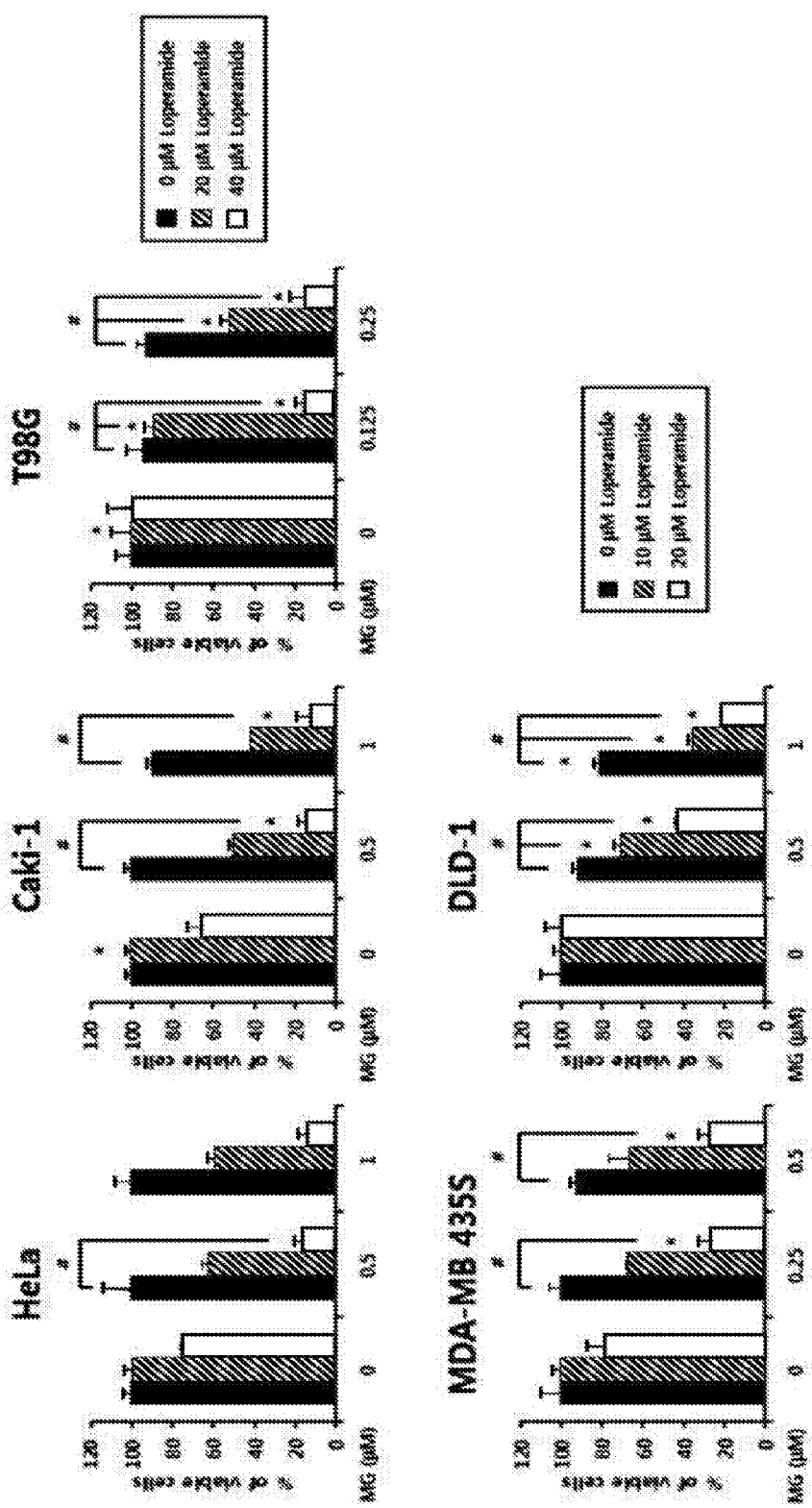
FIG. 10 shows the results of cell viability analysis to confirm the anticancer effect produced by co-administration of MG132 (MG) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 11:
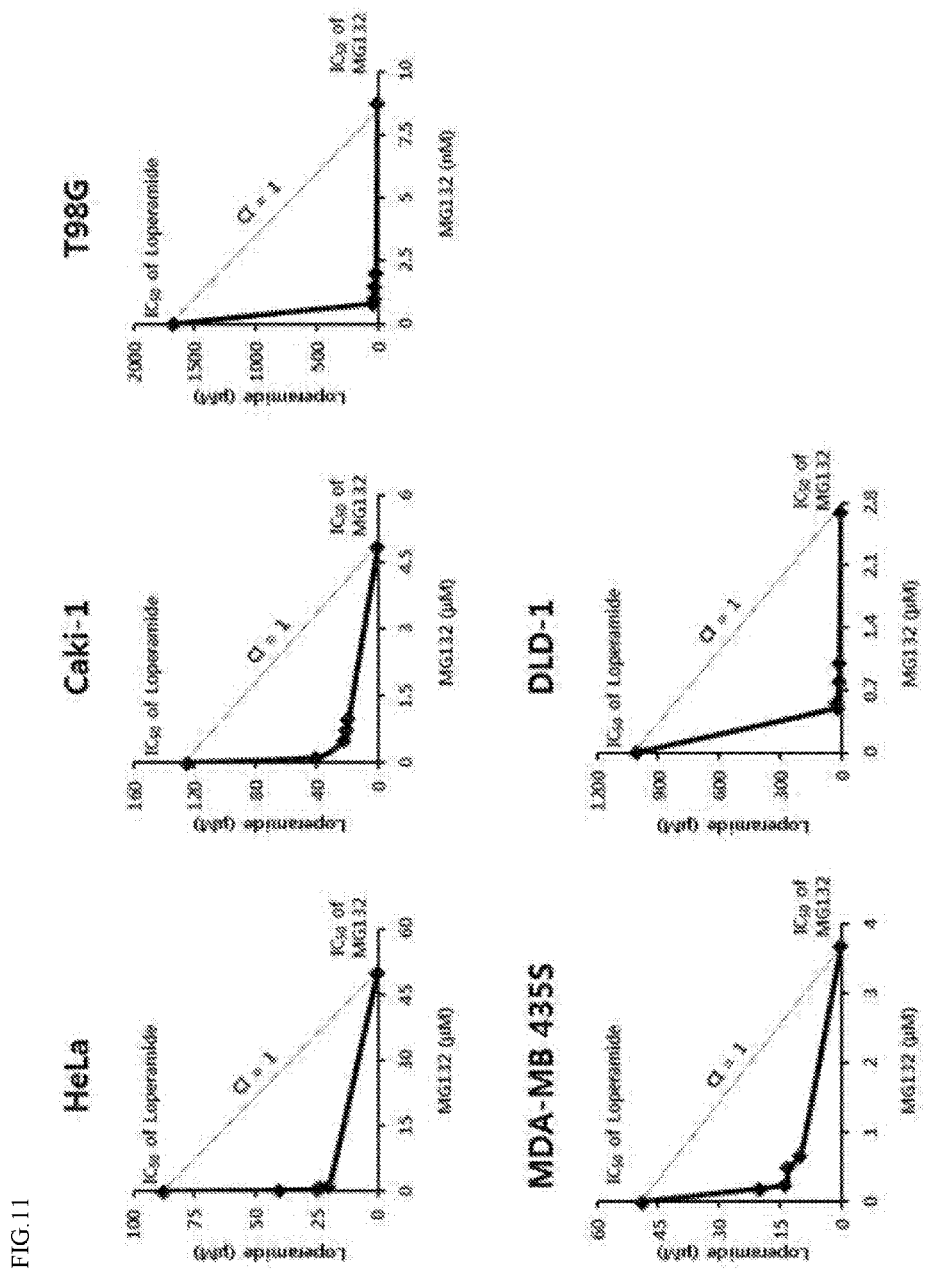
FIG. 11 shows the results of isobologram analysis to confirm the anticancer effect produced by co-administration of MG132 and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 5 Confirmation of Anticancer Effect Following to Combined Administration of MG132 and Loperamide on Solid Cancer Cells HeLa, Caki-1, T98G, MDA-MB 435S, and DLD-1 cells were each single- or combination-treated with MG132 (MG) and loperamide at concentrations shown in FIG. 10 for 24 hours, and the cell viability was measured by using calcein-acetoxy methylether and ethidium homodimer-1. Then, isobologram analysis with respect to an anticancer effect of combined administration of MG132 and loperamide was performed thereon as shown in FIG. 11.

Referring to the results of cell viability analysis in FIG. 10 and Table 21, the HeLa cells treated with MG132 alone did not exhibit cell toxicity up to a concentration of 1 μM, and the cell viability at a concentration of 40 μM decreased about 25% when treated with loperamide alone; when treated with a combination of MG132 and loperamide, cancer cell death increased drug concentration-dependently and significantly, compared to the case when the HeLa cells were treated with each of the MG132 and loperamide alone.

As shown in Table 22, cell viability of the Caki-1 cells treated with MG132 alone at a concentration of 1 μM decreased about 10%, and the cancer cell viability at a concentration of 40 μM decreased about 35% when treated with loperamide alone; whereas, when treated with a combination of MG132 and loperamide, cancer cell death increased drug concentration-dependently and significantly, compared to the case when the Caki-1 cells were treated with each of the MG132 and loperamide alone.

As shown in Table 23, up to a concentration of 0.25 μM, the T98G cells treated with MG132 did not exhibit significant cancer cell toxicity with respect to loperamide up to a concentration of 20 μM, but when treated with a combination of MG132 and loperamide, cancer cell death increased drug concentration-dependently and significantly, compared to the case when T98G cells were treated with each of the MG132 and loperamide alone. As shown in Table 24, cell viability of MDA-MB 435S cells treated with MG132 alone did not exhibit significant cancer cell toxicity up to a concentration of 0.5 μM, and cell viability at a concentration of 20 μM decreased about 22% when treated with loperamide alone; when treated with a combination of MG132 and loperamide, cancer cell death increased drug concentration-dependently and significantly, compared to the case when the MDA-MB 435S cells were treated with each of the MG132 and loperamide alone.

Referring to Table 25, viability of DLD-1 cells treated with MG132 alone at a concentration of 1 μM decreased about 19%, and DLD-1 cells exhibited more resistance to loperamide-single treatment, but cancer cell death increased drug concentration-dependently and significantly, compared to the case when DLD-1 cells were treated with each of the MG132 and loperamide alone.

Also, in the isobologram analysis results shown in FIG. 11, it may be confirmed that effective cancer cell death was induced in all the tested HeLa, Caki-1, T98G, MDA-MB 435S, and DLD-1 cells when a combination of MG132 and loperamide was used in the treatment. In this regard, it may be confirmed that combined administration of MG132 and loperamide overcame resistance to MG132 and exhibited an improved anticancer effect on various solid cancer cells.

TABLE 21

| HeLa | | | |
|---|---|---|---|
| Loperamide | | Cell viability MG132-added group | |
| concentration | Control group | 0.5 μM | 1 μM |
| 0 μM | 100 | 100 | 100 |
| 20 μM | 99.71 | 62.19 | 59.36 |
| 40 μM | 75.09 | 15.85 | 13.72 |

TABLE 22

| Caki-1 | | | |
|---|---|---|---|
| Loperamide | | Cell viability MG132-added group | |
| concentration | Control group | 0.5 μM | 1 μM |
| 0 μM | 100 | 100 | 89.29 |
| 20 μM | 100 | 50.41 | 41.71 |
| 40 μM | 65.09 | 14.39 | 12.80 |

TABLE 23

| T98G | | | |
|---|---|---|---|
| Loperamide | | Cell viability MG132-added group | |
| concentration | Control group | 0.125 μM | 0.25 μM |
| 0 μM | 100 | 99.69 | 96.53 |
| 10 μM | 100 | 94.79 | 74.57 |
| 20 μM | 99 | 92.44 | 40.53 |

TABLE 24

| MDA-MB 435S | | | |
|---|---|---|---|
| Loperamide | | Cell viability MG132-added group | |
| concentration | Control group | 0.25 μM | 0.5 μM |
| 0 μM | 100 | 100 | 93.03 |
| 10 μM | 100 | 67.74 | 66.41 |
| 20 μM | 77.95 | 26.23 | 27.19 |

TABLE 25

| DLD-1 | | | |
|---|---|---|---|
| Loperamide | | Cell viability MG132-added group | |
| concentration | Control group | 0.5 μM | 1 μM |
| 0 μM | 100 | 91.69 | 81.30 |
| 10 μM | 100 | 70.91 | 35.90 |
| 20 μM | 100 | 43.02 | 21.66 |

Figure 12:
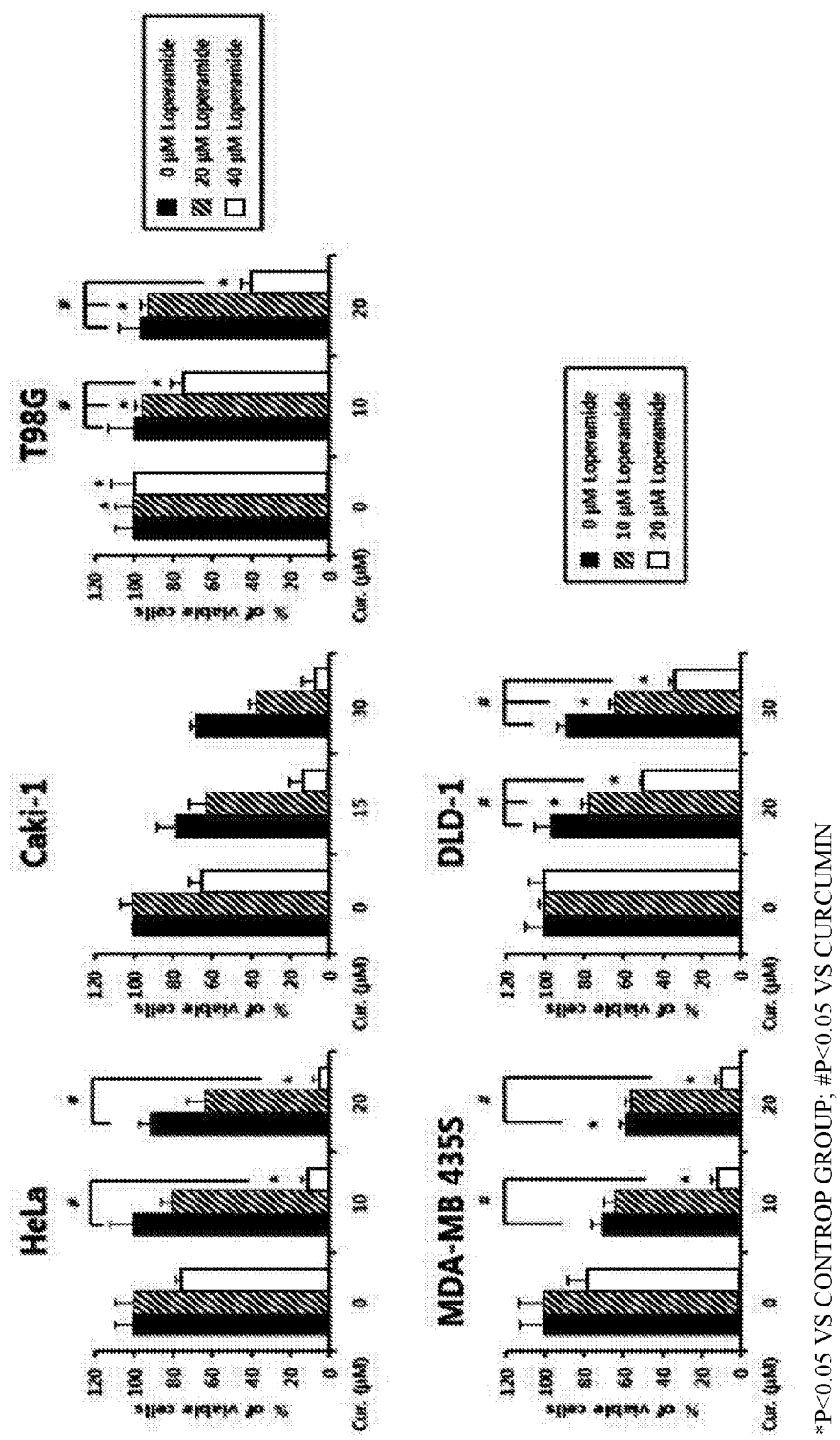
FIG. 12 shows the results of cell viability analysis to confirm the anticancer effect produced by co-administration of curcumin (Cur.) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 13:
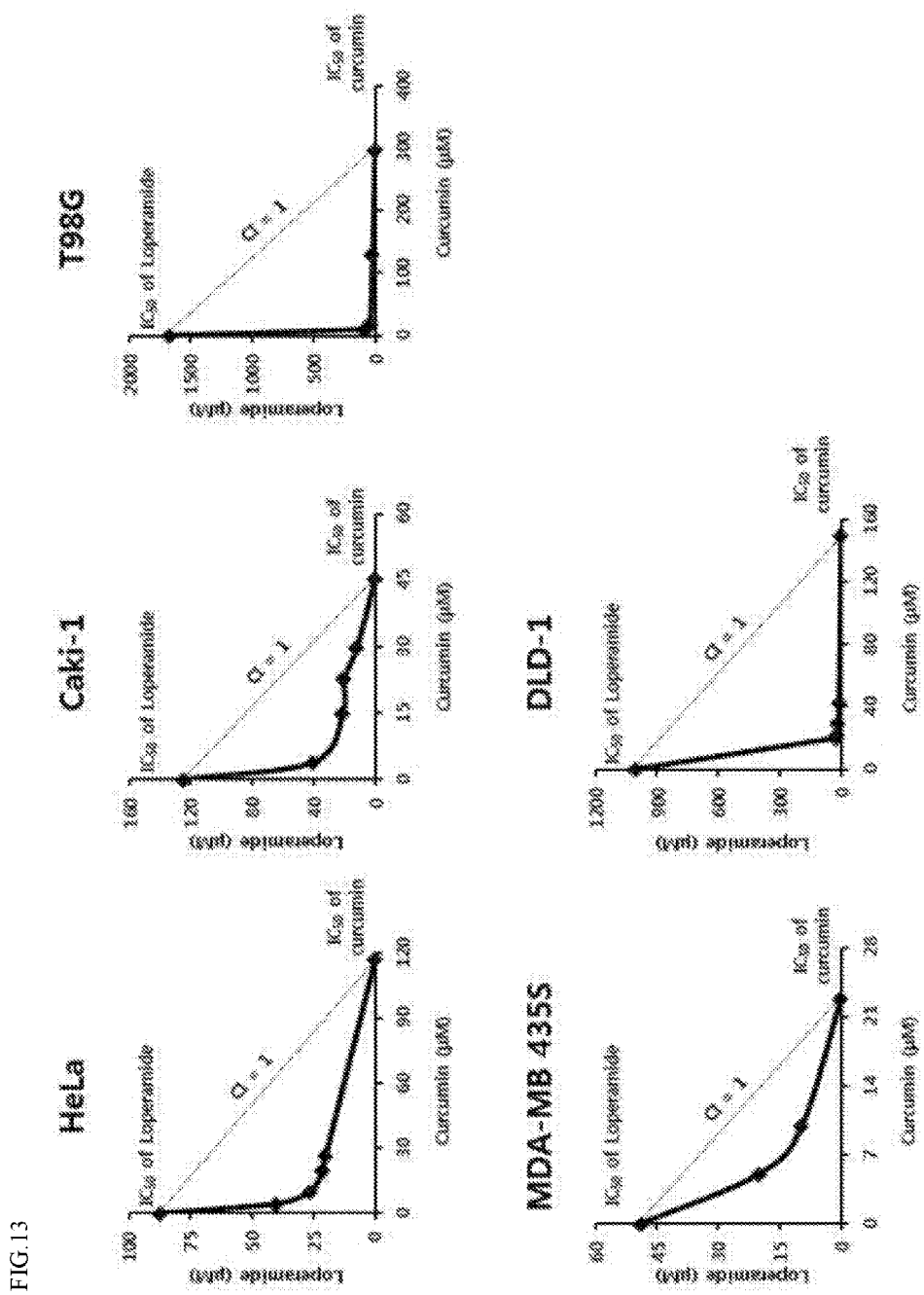
FIG. 13 shows the results of isobologram analysis to confirm the anticancer effect produced by co-administration of curcumin and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 6 Confirmation of Anticancer Effect Following to Combined Administration of Curcumin and Loperamide on Solid Cancer Cells HeLa, Caki-1, T98G, MDA-MB 435S, and DLD-1 cells were each single- or combination-treated with curcumin (Cur.) and loperamide at concentrations shown in FIG. 12 for 24 hours, and the cell viability was measured by using calcein-acetoxy methylether and ethidium homodimer-1. Then, isobologram analysis with respect to an anticancer effect of combined administration of curcumin and loperamide was performed thereon as shown in FIG. 13.

As the results of cell viability analysis shown in Table 26, cell viability of the HeLa cells treated with curcumin alone at a concentration of 20 μM decreased about 9%, and cell viability at a concentration of 40 μM decreased about 25% when treated with loperamide alone; in contrast, when treated with a combination of curcumin and loperamide, cancer cell death increased drug concentration-dependently and significantly, compared to the case when the HeLa cells was treated with each of the curcumin and loperamide alone.

As shown in Table 27, cell viability of the Caki-1 cells treated with curcumin alone at a concentration of 30 μM decreased about 32%, and the cell viability at a concentration of 40 μM decreased about 35% when treated with loperamide alone; in contrast, when treated with a combination of curcumin and loperamide, cancer cell death increased drug concentration-dependently and significantly, compared to the case when the Caki-1 cells were treated with each of the curcumin and loperamide alone.

Also, referring to Table 28, cell viability of the T98G cells treated with curcumin alone almost did not decrease at a concentration of 20 μM and did not exhibit significant cancer cell toxicity with respect to loperamide up to a concentration of 20 μM, but when treated with a combination of curcumin and loperamide, cancer cell death increased drug concentration-dependently and significantly, compared to the case when the T98G cells were treated with each of the curcumin and loperamide alone.

Also, referring to Table 29, cell viability of the MDA-MB 435S cells treated with curcumin alone at a concentration of 20 μM decreased about 41%, and the cancer cell viability at a concentration of 20 μM decreased about 22% when treated with loperamide alone; in contrast, when treated with a combination of curcumin and loperamide, cancer cell death increased drug concentration-dependently and significantly, compared to the case when the MDA-MB 435S cells were treated with each of the curcumin and loperamide alone. As shown in Table 30, DLD-1 cells exhibited more resistance to curcumin-single treatment and loperamide-single treatment compared to other cancer cells, but when treated with a combination of curcumin and loperamide, cancer cell death increased drug concentration-dependently and significantly, compared to the case when DLD-1 cells were treated with each of the curcumin and loperamide alone.

Also, in the isobologram analysis results shown in FIG. 13, it may be confirmed that effective cancer cell death was induced in all the HeLa, Caki-1, T98G, MDA-MB 435S, and DLD-1 cells when a combination of the curcumin and loperamide was used in the treatment. In this regard, it may be confirmed that combined administration of curcumin and loperamide overcame resistance to curcumin and exhibited an improved anticancer effect on various solid cancer cells.

TABLE 26

| HeLa | | | |
|---|---|---|---|
| Loperamide | | Cell viability Curcumin-added group | |
| concentration | Control group | 10 μM | 20 μM |
| 0 μM | 100 | 100 | 91.29 |
| 20 μM | 99.71 | 80.70 | 63.14 |
| 40 μM | 75.09 | 11.58 | 4.46 |

TABLE 27

| Caki-1 | | | |
|---|---|---|---|
| Loperamide | | Cell viability Curcumin-added group | |
| concentration | Control group | 15 μM | 30 μM |
| 0 μM | 100 | 78.52 | 68.22 |
| 20 μM | 100 | 62.23 | 36.70 |
| 40 μM | 65.09 | 14.01 | 7.58 |

TABLE 28

| T98G | | | |
|---|---|---|---|
| Loperamide | | Cell viability Curcumin-added group | |
| concentration | Control group | 10 μM | 20 μM |
| 0 μM | 100 | 99.69 | 96.53 |
| 10 μM | 100 | 94.79 | 74.57 |
| 20 μM | 99 | 96.53 | 40.53 |

TABLE 29

| MDA-MB 435S | | | |
|---|---|---|---|
| Loperamide | | Cell viability Curcumin-added group | |
| concentration | Control group | 10 μM | 20 μM |
| 0 μM | 100 | 70.73 | 58.80 |
| 10 μM | 100 | 63.42 | 56.40 |
| 20 μM | 77.95 | 11.44 | 9.72 |

TABLE 30

| DLD-1 | | | |
|---|---|---|---|
| Loperamide | | Cell viability Curcumin-added group | |
| concentration | Control group | 20 μM | 30 μM |
| 0 μM | 100 | 96.73 | 89.02 |
| 10 μM | 100 | 77.74 | 64.50 |
| 20 μM | 100 | 50.14 | 33.82 |

Figure 14:
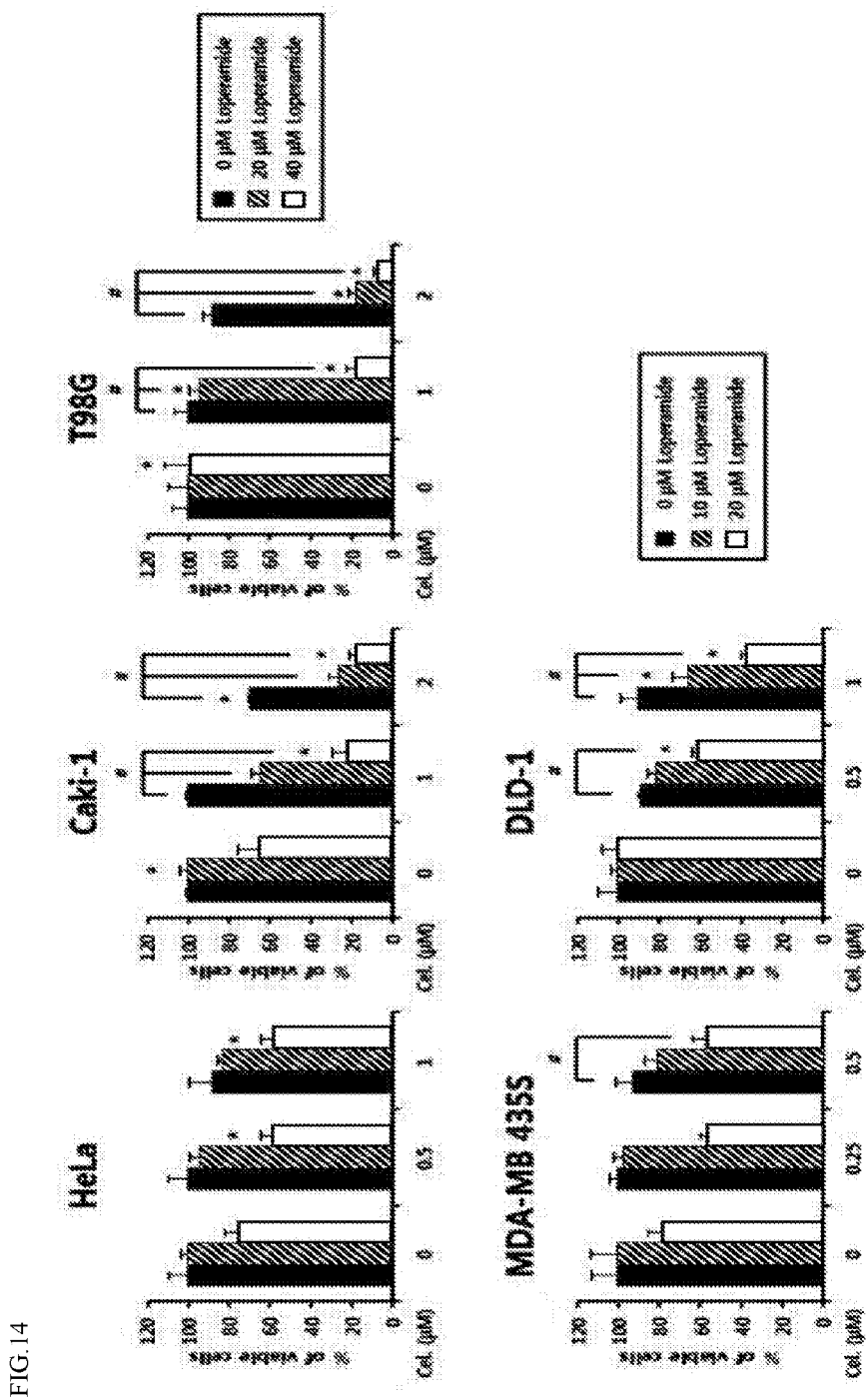
FIG. 14 shows the results of cell viability analysis to confirm the anticancer effect produced by co-administration of celastrol (Cel.) and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)
Figure 15:
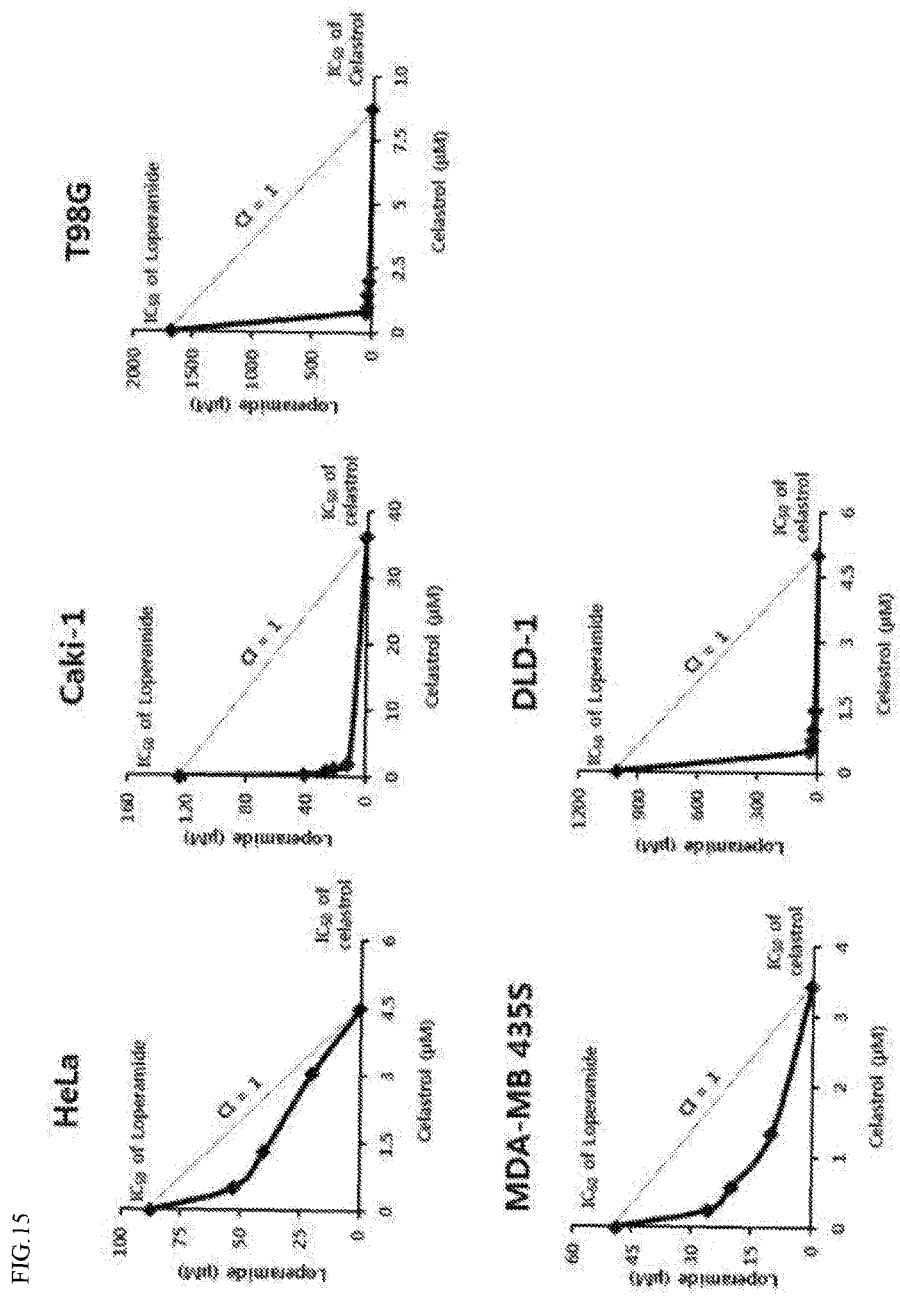
FIG. 15 shows the results of isobologram analysis to confirm the anticancer effect produced by co-administration of celastrol and loperamide, according to the present invention, in solid cancer cells such as cervical cancer cell (HeLa), kidney cancer cell (Caki-1), brain tumor cell (T98G), breast cancer cell (MDA-MB 435S), and colon cancer cell (DLD-1)

Example 7 Confirmation of Anticancer Effect Following to Combined Administration of Celastrol and Loperamide on Solid Cancer Cells HeLa, Caki-1, T98G, MDA-MB 435S, and DLD-1 cells were each single- or combination-treated with celastrol and loperamide at concentrations shown in FIG. 14 for 24 hours, and the cell viability was measured by using calcein-acetoxy methylether and ethidium homodimer-1. Then, isobologram analysis with respect to an anticancer effect of combined administration of celastrol and loperamide was performed thereon as shown in FIG. 15.

Referring to the results of cell viability analysis in FIG. 14 and Table 31, viability the HeLa cells treated with celastrol alone decreased about 11% at a concentration of 1 μM, and the cancer cell viability at a concentration of 40 μM decreased about 25% when treated with loperamide alone; whereas, when treated with a combination of celastrol and loperamide, cancer cell death increased drug concentration-dependently and significantly, compared to the case when the HeLa cells were treated with each of the celastrol and loperamide alone.

Also, as shown in Table 32, Caki-1 cells treated with celastrol alone did not induce cancer cell toxicity up to 1 μM, a cancer cell viability of the Caki-1 cell decreased about 30% at a concentration of 2 μM, and the cancer cell viability at a concentration of 40 μM decreased about 35% when treated with loperamide alone; whereas, when treated with a combination of celastrol and loperamide, cancer cell death increased drug concentration-dependently and significantly, compared to the case when the Caki-1 cells were treated with each of the celastrol and loperamide alone.

As shown in Table 33, cell viability of T98G cells treated with celastrol alone at a concentration of 2 μM decreased about 9%, and the cancer cell viability at a concentration of 20 μM decreased about 10% when treated with loperamide alone; in contrast, when treated with a combination of celastrol and loperamide, cancer cell death increased drug concentration-dependently and significantly, compared to the case when T98G cells were treated with each of the celastrol and loperamide alone.

As shown in Table 34, cell viability of MDA-MB 435S cells treated with celastrol alone at a concentration of 0.5 μM decreased about 7%, and the cancer cell viability at a concentration of 20 μM decreased about 22% when treated with loperamide alone; in contrast, when treated with a combination of celastrol and loperamide, cancer cell death increased drug concentration-dependently and significantly, compared to the case when MDA-MB 435S cells were treated with each of the celastrol and loperamide alone.

As shown in Table 35, cell viability of DLD-1 cells treated with celastrol alone at a concentration of 1 μM decreased about 11%, and DLD-1 cells treated with loperamide alone exhibited more resistance compared to other cancer cells, but when treated with a combination of celastrol and loperamide, cancer cell death increased drug concentration-dependently and significantly, compared to the case when DLD-1 cells were treated with each of the celastrol and loperamide alone.

Also, in the isobologram analysis results shown in FIG. 15, it may be confirmed that effective cancer cell death was induced in all the treated HeLa, Caki-1, T98G, MDA-MB 435S, and DLD-1 cells when a combination of the celastrol and loperamide was used in the treatment. In this regard, it may be confirmed that combined administration of celastrol and loperamide overcame resistance to celastrol and exhibited an improved anticancer effect on various solid cancer cells.

TABLE 31

HeLa

| Loperamide concentration | Control group | Cell viability Celastrol-added group | |
|---|---|---|---|
| | | 0.5 μM | 1 μM |
| 0 μM | 100 | 100 | 88.43 |
| 20 μM | 99.71 | 93.83 | 83.14 |
| 40 μM | 75.09 | 58.25 | 58.15 |

TABLE 32

Caki-1

| Loperamide concentration | Control group | Cell viability Celastrol-added group | |
|---|---|---|---|
| | | 1 μM | 2 μM |
| 0 μM | 100 | 100 | 69.63 |
| 20 μM | 100 | 64.54 | 26.74 |
| 40 μM | 65.09 | 21.67 | 17.22 |

TABLE 33

T98G

| Loperamide concentration | Control group | Cell viability Celastrol-added group | |
|---|---|---|---|
| | | 1 μM | 2 μM |
| 0 μM | 100 | 100 | 91.34 |
| 10 μM | 94.43 | 86 | 64.64 |
| 20 μM | 90.40 | 54.90 | 33.26 |

TABLE 34

MDA-MB 435S

| Loperamide concentration | Control group | Cell viability Celastrol-added group | |
|---|---|---|---|
| | | 0.25 μM | 0.5 μM |
| 0 μM | 100 | 100 | 92.54 |
| 10 μM | 100 | 97.11 | 80.34 |
| 20 μM | 77.95 | 56.08 | 56.97 |

TABLE 35

DLD-1

| Loperamide concentration | Control group | Cell viability Celastrol-added group | |
|---|---|---|---|
| | | 0.5 μM | 1 μM |
| 0 μM | 100 | 90.50 | 88.72 |
| 10 μM | 100 | 81.30 | 65.28 |
| 20 μM | 100 | 60.83 | 37.09 |

Example 8 Confirmation of Anticancer Effect Following to Combined Administration of Various Proteasome Inhibitor and Loperamide in Multiple Myeloma Cells Experiments to test an effect of single or combined treatment of bortezomib, carfilzomib, MLN9708, epoxomicin, MG132, curcumin, or celastrol, as a proteasome inhibitor and loperamide on multiple myeloma cells were performed.

Figure 16:
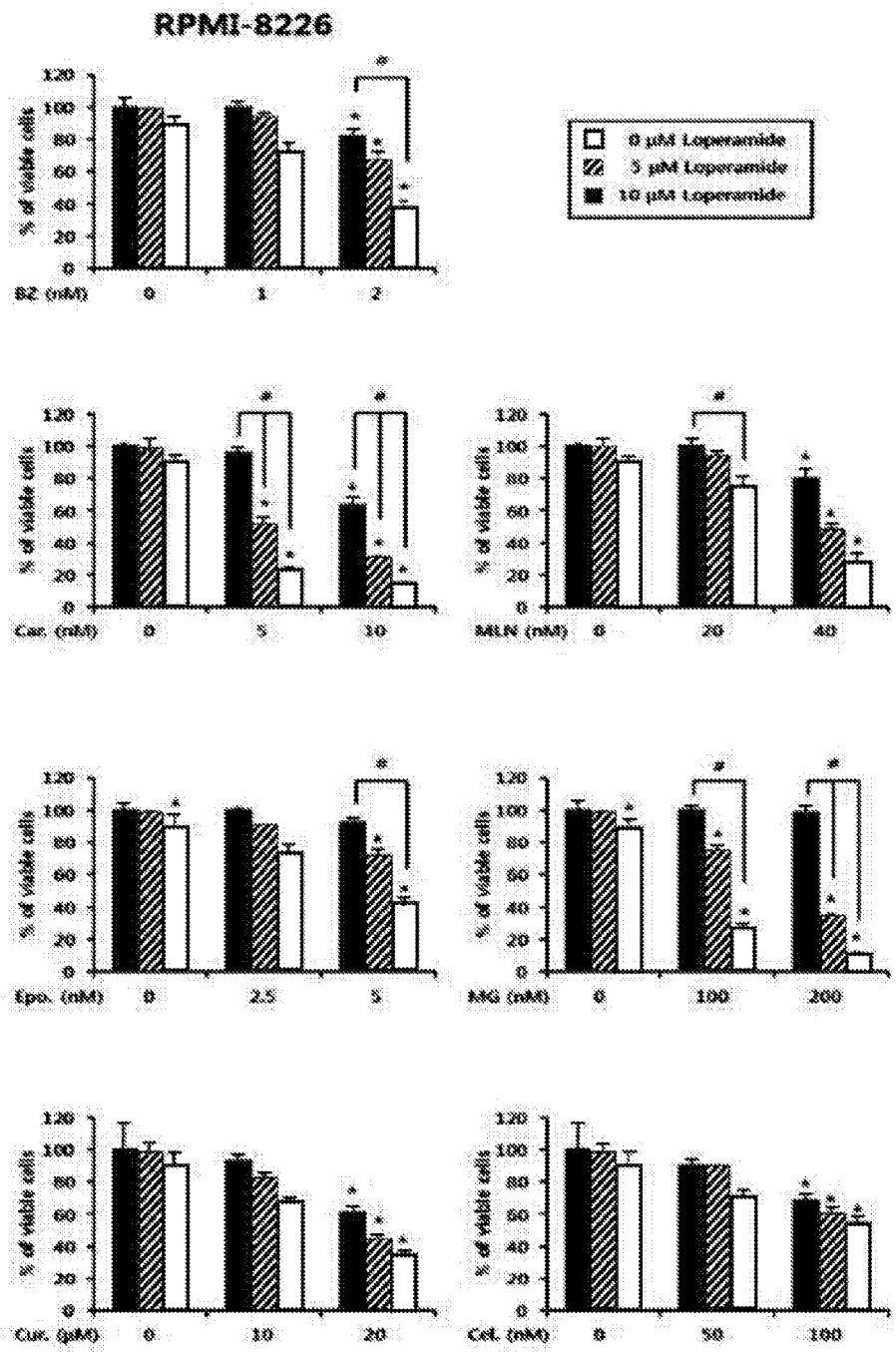
FIG. 16 shows the results of cell viability analysis to confirm the effect on multiple myeloma cells (RPMI-8226) produced by co-administration of bortezomib (BZ) and loperamide, carfilzomib (Car.) and loperamide, MLN9708 (MLN) and loperamide, epoxomicin (Epo.) and loperamide, MG132 (MG) and loperamide, curcumin (Cur.) and loperamide, or celastrol (Cel.) and loperamide, according to the present invention.

RPMI-8226 cells were treated with bortezomib (BZ) and loperamide, carfilzomib (Car.) and loperamide, MLN9708 (MLN) and loperamide, epoxomicin (Epo.) and loperamide, MG132 (MG) and loperamide, curcumin (Cur.) and loperamide, or celastrol (Cel.) and loperamide alone or as a combination at concentrations shown in FIG. 16 for 24 hours, and the cell viability was measured by using calcein-acetoxy methylether and ethidium homodimer-1. Then, isobologram analysis was performed thereon as shown in FIG. 17.

Tables 36 to 42 show cell viability after single- and combination-treatment at the concentrations of the drugs. As shown in Tables 36 to 42, when the multiple myeloma cells RPMI-8226 were treated with the proteasome inhibitor or loperamide at the shown concentration, the cell viability did not significantly decrease; in contrast, when the cells were treated with a combination with loperamide, cancer cell death increased drug concentration-dependently.

Figure 17:
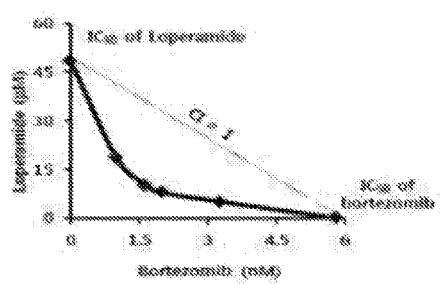
FIG. 17 shows the results of isobologram analysis to confirm the effect on multiple myeloma cells (RPMI-8226) produced by co-administration of bortezomib (BZ) and loperamide, carfilzomib (Car.) and loperamide, MLN9708 (MLN) and loperamide, epoxomicin (Epo.) and loperamide, MG132 (MG) and loperamide, curcumin (Cur.) and loperamide, or celastrol (Cel.) and loperamide, according to the present invention.
Figure 17:
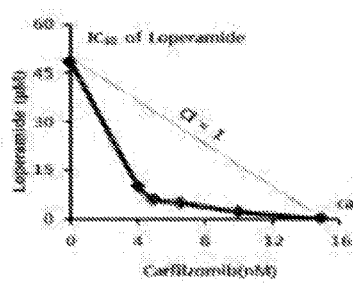
Figure 17:
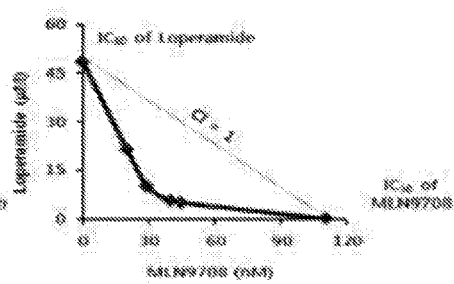
Figure 17:
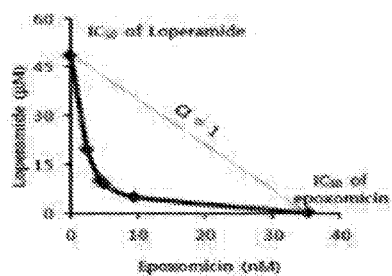
Figure 17:
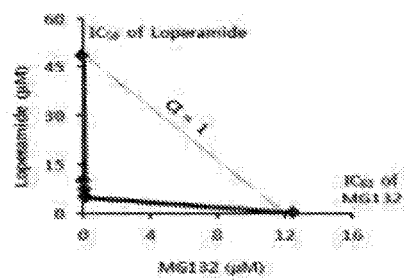
Figure 17:
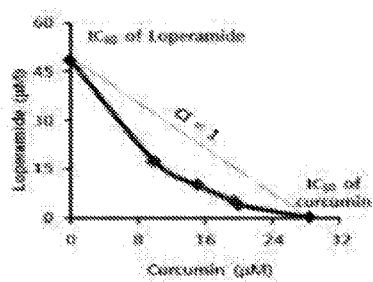
Figure 17:
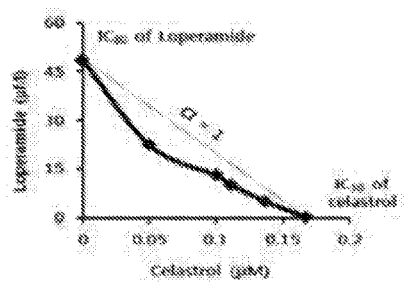

Also, as shown in the isobologram analysis of FIG. 17, when a combination of the proteasome inhibitor and loperamide was used in the treatment, a synergetic effect in the RPMI-8226 cells was confirmed, and cancer cell death was induced. In this regard, it was confirmed that combined administration of a proteasome inhibitor and loperamide overcame resistance to the proteasome inhibitor and improved an anticancer effect on multiple myeloma cells.

TABLE 36

RPMI-8226

| Loperamide concentration | Control group | Cell viability Bortezomib-added group | |
|---|---|---|---|
| | | 1 nM | 2 nM |
| 0 μM | 100 | 100 | 81.70 |
| 5 μM | 98.64 | 94.07 | 71.56 |
| 10 μM | 89.40 | 71.56 | 38.21 |

TABLE 37

RPMI-8226

| Loperamide concentration | Control group | Cell viability Carfilzomib-added group | |
|---|---|---|---|
| | | 5 nM | 10 nM |
| 0 μM | 100 | 95.84 | 63.41 |
| 5 μM | 98.64 | 51.67 | 30.75 |
| 10 μM | 89.40 | 23.98 | 15.19 |

TABLE 38

RPMI-8226

| Loperamide concentration | Control group | Cell viability MLN9708-added group | |
|---|---|---|---|
| | | 20 nM | 40 nM |
| 0 μM | 100 | 100 | 80.85 |
| 5 μM | 98.64 | 95.54 | 48.78 |
| 10 μM | 89.40 | 75.53 | 27.84 |

TABLE 39

RPMI-8226

| Loperamide concentration | Control group | Cell viability Epoxomicin-added group | |
|---|---|---|---|
| | | 2.5 nM | 5 nM |
| 0 μM | 100 | 100 | 92.72 |
| 5 μM | 98.64 | 90.29 | 72.08 |
| 10 μM | 89.40 | 73.85 | 42.55 |

TABLE 40

RPMI-8226

| Loperamide concentration | Control group | Cell viability MG132-added group | |
|---|---|---|---|
| | | 100 nM | 200 nM |
| 0 μM | 100 | 100 | 99.11 |
| 5 μM | 98.64 | 74.91 | 34.15 |
| 10 μM | 89.40 | 27.49 | 11.29 |

TABLE 41

RPMI-8226

| Loperamide concentration | Control group | Cell viability Curcumin-added group | |
|---|---|---|---|
| | | 10 μM | 20 μM |
| 0 μM | 100 | 93.64 | 61.85 |
| 5 μM | 98.64 | 82.73 | 45.04 |
| 10 μM | 89.40 | 67.92 | 34.56 |

| Loperamide concentration | Control group | Cell viability Celastrol-added group | |
|---|---|---|---|
| | | 50 nM | 100 nM |
| 0 μM | 100 | 90.71 | 68.98 |
| 5 μM | 98.64 | 89.56 | 71.15 |
| 10 μM | 89.40 | 71.15 | 54.70 |

Example 9 Confirmation of Anticancer Effect Following to Combined Administration of Bortezomib and Loperamide on Normal Breast Epithelial Cells Experiments to test an effect of single or combined treatment of bortezomib, carfilzomib, MLN9708, epoxomicin, MG132, curcumin, or celastrol, as a proteasome inhibitor and loperamide on normal breast epithelial cells were performed.

Figure 18:
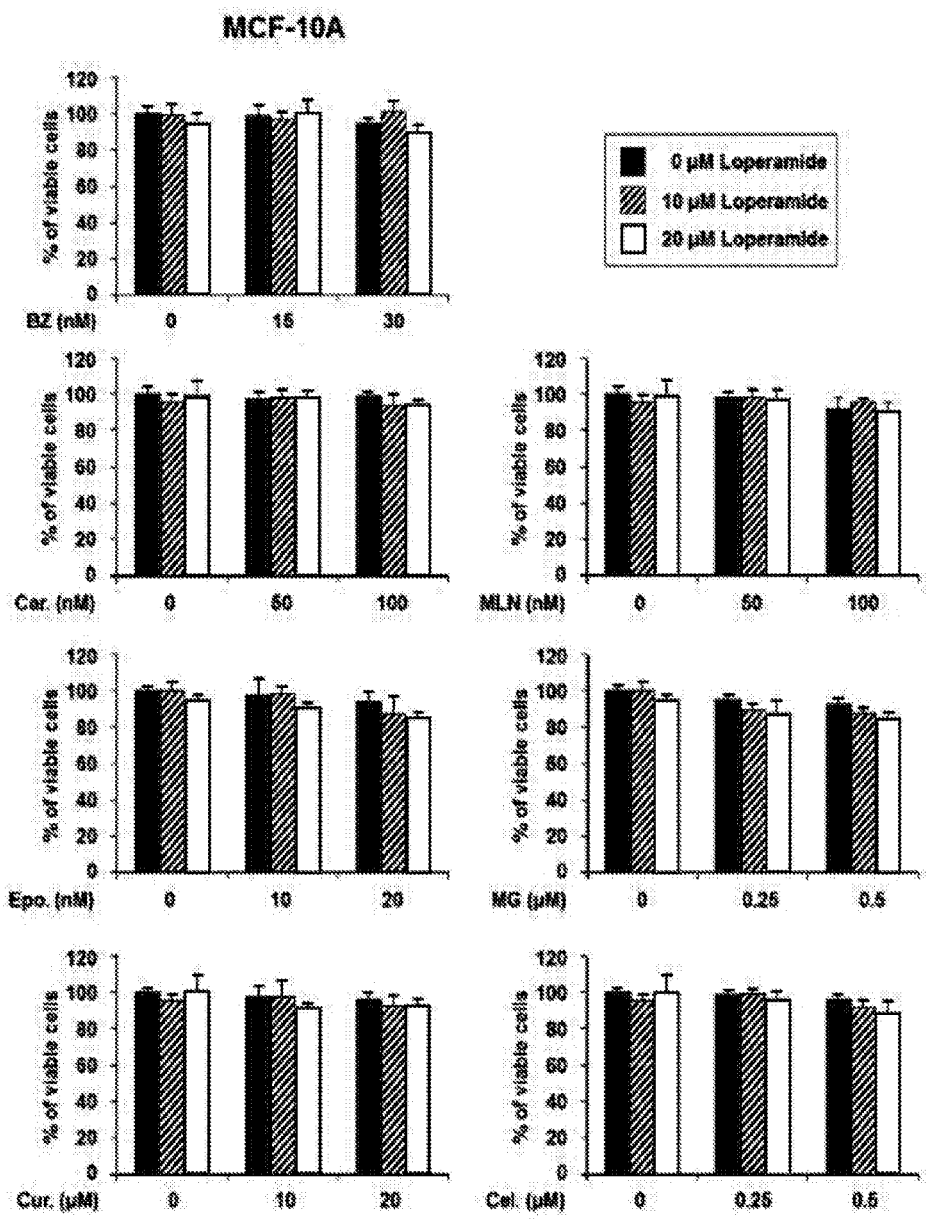
FIG. 18 shows the results of cell viability analysis to confirm the effect on normal breast epithelial cells produced by co-administration of bortezomib (BZ) and loperamide, carfilzomib (Car.) and loperamide, MLN9708 (MLN) and loperamide, epoxomicin (Epo.) and loperamide, MG132 (MG) and loperamide, curcumin (Cur.) and loperamide, or celastrol (Cel.) and loperamide, according to the present invention.

MCF-10A cells were treated with bortezomib (BZ) and loperamide, carfilzomib (Car.) and loperamide, MLN9708 (MLN) and loperamide, epoxomicin (Epo.) and loperamide, MG132 (MG) and loperamide, curcumin (Cur.) and loperamide, or celastrol (Cel.) and loperamide alone or as a combination at concentrations shown in FIG. 18 for 24 hours, and the cell viability was measured by using calcein-acetoxy methylether and ethidium homodimer-1. Tables 43 to 49 show cell viability after single- or combination-treatment of the drugs.

As the results shown in FIG. 18, it was confirmed that single- or combination-treatment of the proteasome inhibitors and loperamide almost did not induce cell death in the normal breast epithelial cells. Also, referring to the results, it was confirmed that the combined-treatment of each of the proteasome inhibitors and loperamide exhibited safety in normal cells and selectively induced cancer cell death.

TABLE 43

MCF-10A

| Loperamide concentration | Control group | Cell viability Bortezomib-added group | |
|---|---|---|---|
| | | 15 nM | 30 nM |
| 0 μM | 100 | 98.85 | 94.63 |
| 10 μM | 97.70 | 96.63 | 100.76 |
| 20 μM | 94.63 | 100.38 | 89.27 |

TABLE 44

MCF-10A

| Loperamide concentration | Control group | Cell viability Carfilzomib-added group | |
|---|---|---|---|
| | | 50 nM | 100 nM |
| 0 μM | 100 | 99.54 | 98.13 |
| 10 μM | 95.21 | 98.41 | 93.29 |
| 20 μM | 99.25 | 98.72 | 94.02 |

TABLE 45

MCF-10A

| Loperamide concentration | Control group | Cell viability MLN9708-added group | |
|---|---|---|---|
| | | 50 nM | 100 nM |
| 0 μM | 100 | 98.04 | 92.32 |
| 10 μM | 95.21 | 98.42 | 95.26 |
| 20 μM | 99.25 | 96.83 | 90.41 |

TABLE 46

MCF-10A

| Loperamide concentration | Control group | Cell viability Epoxomicin-added group | |
|---|---|---|---|
| | | 10 nM | 20 nM |
| 0 μM | 100 | 97.62 | 94.36 |
| 10 μM | 100.29 | 98.21 | 87.24 |
| 20 μM | 94.65 | 90.50 | 84.56 |

TABLE 47

MCF-10A

| Loperamide concentration | Control group | Cell viability MG132-added group | |
|---|---|---|---|
| | | 0.25 μM | 0.5 μM |
| 0 μM | 100 | 95.25 | 92.87 |
| 10 μM | 100.29 | 89.11 | 87.92 |
| 20 μM | 94.65 | 88.13 | 84.43 |

TABLE 48

MCF-10A

| Loperamide concentration | Control group | Cell viability Curcumin-added group | |
|---|---|---|---|
| | | 10 μM | 20 μM |
| 0 μM | 100 | 97.74 | 95.86 |
| 10 μM | 95.11 | 97.36 | 92.85 |
| 20 μM | 100.37 | 91.72 | 92.48 |

TABLE 49

MCF-10A

| Loperamide concentration | Control group | Cell viability Celastrol-added group | |
|---|---|---|---|
| | | 0.25 μM | 0.5 μM |
| 0 μM | 100 | 98.87 | 95.86 |
| 10 μM | 95.11 | 99.62 | 92.10 |
| 20 μM | 100.37 | 95.48 | 88.34 |

Hereinafter, formulation examples of a pharmaceutical composition according to the present invention will be described, but the examples are not intended to limit the present invention but simple to describe the present invention in detail.

Formulation Example 1 Preparation of Injection 3.5 mg of bortezomib, 4 mg of loperamide, 3.0 mg of sodium metabisulfate, 0.8 mg of methylparaben, 0.1 mg of propylparaben, and an appropriate amount of sterile distilled water for injection were mixed by using a general method so that a final volume was 2 ml, and the mixture was filled in an ampoule having a capacity of 2 ml and sterilized to prepare an injection.

Formulation Example 2 Preparation of Tablets 3.5 mg of bortezomib, 4 mg of loperamide, 100 mg of lactose, 100 mg of starch, and an appropriate amount of magnesium stearate were mixed, and the mixture was prepared into tablets according to a general tablet preparation method.

Formulation Example 2 Preparation of Capsules 3.5 mg of bortezomib, 4 mg of loperamide, 50 mg of lactose, 50 mg of starch, 2 mg of talc, and an appropriate amount of magnesium stearate were mixed, and the mixture was filled in gelatin capsules to prepare capsules according to a general capsule preparation method.

INDUSTRIAL APPLICABILITY

When a proteasome inhibitor of a low concentration is used in a patient with blood cancer, side effects of the proteasome inhibitor may be reduced, and the proteasome inhibitor may be used in various types of blood cancers. Particularly, the proteasome inhibitor may effectively induce cancer cell death in solid cancer which has not exhibited an anticancer effect with respect to the proteasome inhibitor, such as bortezomib. Thus, a composition containing a proteasome inhibitor and loperamide as active ingredients, according to the present invention, can be useful for preventing or treating cancer, and loperamide can be provided as an anticancer supplement when the proteasome inhibitor is used to treat cancer.

The invention claimed is:

1. A method of treating cancer in a subject in need thereof, comprising:
providing a pharmaceutical composition comprising a proteasome inhibitor and loperamide as active ingredients; and
administering the pharmaceutical composition to the subject,
wherein the cancer is treated,
wherein the loperamide reduces resistance of cancer cells to the proteasome inhibitor and improves anticancer effect of the proteasome inhibitor.

2. The method of claim 1 comprising the proteasome inhibitor ranging from about 1 wt % to about 50 wt % and the loperamide ranging from about 50 wt % to about 99 wt %.

3. The method of claim 1, wherein the proteasome inhibitor is selected from the group consisting of bortezomib, carfilzomib, MLN9708, epoxomicin, MG132, curcumin, and celastrol.

4. The method of claim 1, wherein the cancer is selected from the group consisting of solid cancer and blood cancer.

5. The method of claim 4, wherein the solid cancer is selected from the group consisting of cervical cancer, kidney cancer, brain tumor, breast cancer, and colon cancer.

6. The method of claim 4, wherein the blood cancer is selected from the group consisting of leukemia, myeloma, and malignant lymphoma.

7. A method of enhancing cancer cell death, the method comprising co-administering a proteasome inhibitor and loperamide to cancer cells,
wherein the loperamide reduces resistance of the cancer cells to the proteasome inhibitor and improves anticancer effect of the proteasome inhibitor.

* * * * *